(12) United States Patent
Kanemura et al.

(10) Patent No.: US 6,503,865 B1
(45) Date of Patent: Jan. 7, 2003

(54) METHOD OF PREPARING PENTAFLUOROETHANE, CATALYSTS FOR FLUORINATION AND A PREPARATION METHOD THEREOF

(75) Inventors: Takashi Kanemura, Settsu (JP); Takashi Shibanuma, Settsu (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 10/172,970

(22) Filed: Jun. 18, 2002

Related U.S. Application Data

(62) Division of application No. 09/581,285, filed on Jun. 12, 2000, now Pat. No. 6,433,233.

(30) Foreign Application Priority Data

Dec. 12, 1997 (JP) .............................................. 9-342774

(51) Int. Cl.[7] .......................... B01J 27/06; B01J 27/132; B01J 23/00
(52) U.S. Cl. ........................ 502/224; 502/228; 502/307; 502/314; 502/315; 502/320
(58) Field of Search ................................ 502/224, 228, 502/307, 314, 315, 320

(56) References Cited

U.S. PATENT DOCUMENTS 4,792,643 A 12/1988 Sobolev
6,403,524 B2 * 6/2002 Scott et al.

* cited by examiner

Primary Examiner—Alan Siegel
(74) Attorney, Agent, or Firm—Armstrong, Westerman & Hattori, LLP

(57) ABSTRACT

A method of preparing pentafluoroethane wherein chlorine-containing carbon compounds are fluorinated in the presence of chromium catalysts that are in an amorphous state and wherein the main component is chromium compounds with the addition of at least one metal element selected from the group composed of indium, gallium, cobalt, nickel, zinc and aluminum and the average valence of the chromium in said chromium compounds is not less than +3.5 but not more than +5.0. And said chromium catalysts and a preparation method thereof.

A method of preparing pentafluoroethane wherein the total yield of chlorofluoroethane by-products can be decreased without significantly deteriorating the generation activity of the pentafluoroethane and compounds which can be recycled in the reaction system. And to provide catalysts for this fluorination and a preparation method thereof.

10 Claims, 11 Drawing Sheets

FIG.1

CATALYST PREPARATION EXAMPLE (CATALYSTS 1-6: IMPREGNATION METHOD)

(CHROMIUM NITRATE) + (AMMONIUM HYDROXIDE)
↓
PRECIPITATE OF CHROMIUM HYDROXIDE
↓
FILTRATION · WASHING WITH WATER
↓
DRYING AT 120 °C FOR 2 HR
↓
GRINDING UP TO NOT MORE THAN 0.2 mm IN PARTICLE SIZE

| In(NO$_3$)$_3$ · 3H$_2$O | Ga(NO$_3$)$_3$ · 8H$_2$O | Co(NO$_3$)$_2$ · 6H$_2$O | Ni(NO$_3$)$_2$ · 6H$_2$O | Zn(NO$_3$)$_2$ · 6H$_2$O | Al(NO$_3$)$_3$ · 9H$_2$O |
|---|---|---|---|---|---|
| CATALYST 1 | CATALYST 2 | CATALYST 3 | CATALYST 4 | CATALYST 5 | CATALYST 6 |

IMMERSED IN EACH AQUEOUS SOLUTION AND ALLOWED TO STAND FOR 12 HR
↓
DRYING · GRINDING
↓
GRAPHITE ADDITION
↓
COMPRESSION MOLDING
↓
CONTACT IN NITROGEN AT 400 °C FOR 2 HR (CALCINATION)
↓
CONTACT IN HF GAS + NITROGEN GAS AT 200-360 °C FOR 2 HR (FLUORINATION)
↓
CATALYSTS 1-6

FIG.3

CATALYST PREPARATION EXAMPLE (COMPARATIVE CATALYSTS 1-3)

(CHROMIUM NITRATE) + (AMMONIUM HYDROXIDE)
↓
PRECIPITATE OF CHROMIUM HYDROXIDE
↓
FILTRATION · WASHING WITH WATER
↓
DRYING AT 120 °C FOR 2 HR
↓
GRINDING UP TO NOT MORE THAN 0.2 mm IN PARTICLE SIZE
↓
CONTACT IN $N_2$ GAS AT MORE THAN 550 °C FOR 2 HR (CALCINATION)

<u>COMPARATIVE CATALYST 1</u>

<u>COMPARATIVE CATALYST 2</u>

<u>COMPARATIVE CATALYST 3</u>
↓
IMMERSION IN $In(NO_3)_3 \cdot 3H_2O$
↓
DRYING · GRINDING ↓
GRAPHITE ADDITION
↓
COMPRESSION · MOLDING
↓
CONTACT IN NITROGEN AT 400 °C FOR 2 HR (CALCINATION)
↓
CONTACT IN HF GAS + NITROGEN GAS AT 200-360 °C FOR 2 HR
(FLUORINATION)
↓
COMPARATIVE CATALYSTS 1-3

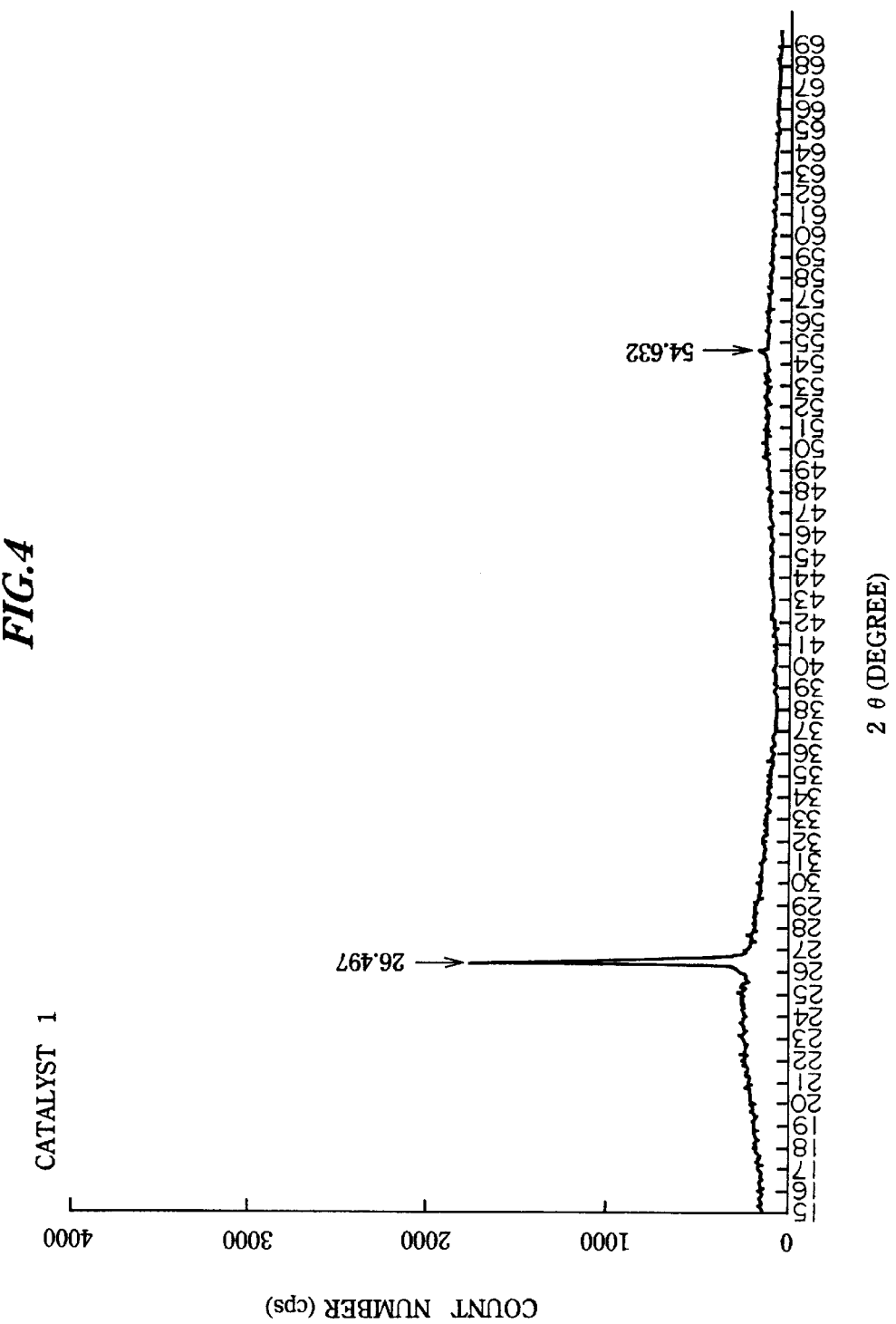

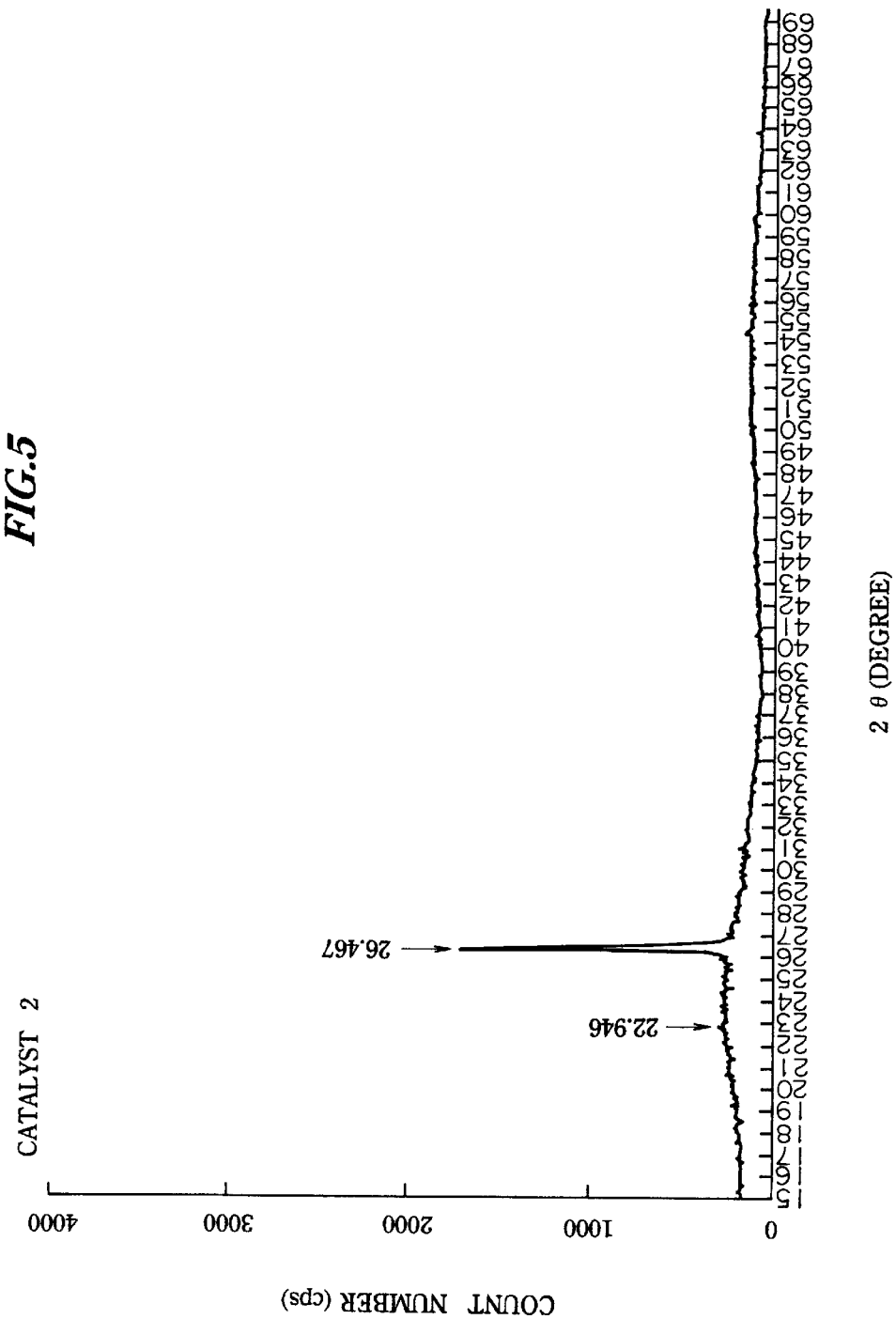

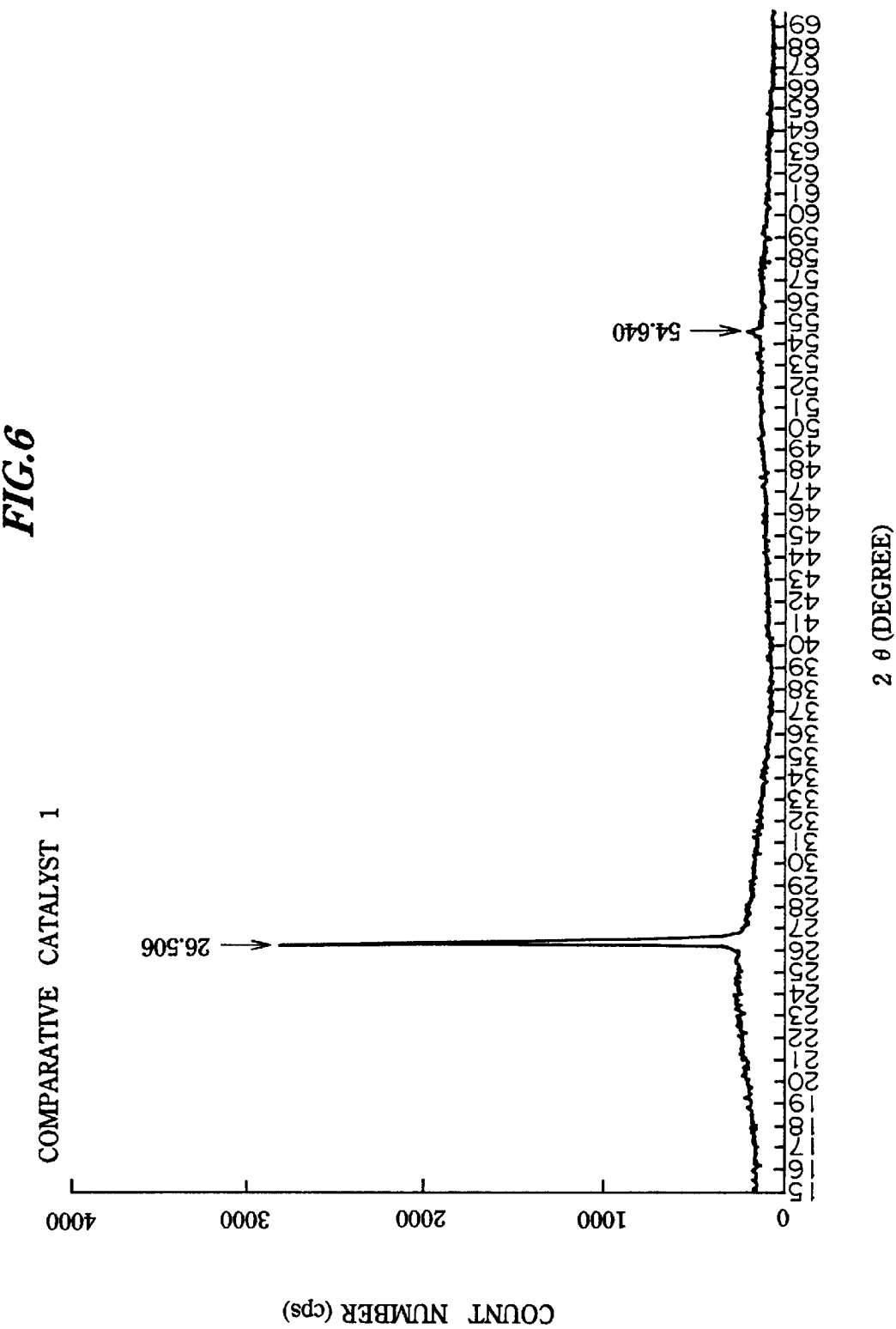

METHOD OF PREPARING PENTAFLUOROETHANE, CATALYSTS FOR FLUORINATION AND A PREPARATION METHOD THEREOF

This application is a divisional of prior application Ser. No. 09/581,285 filed Jun. 12, 2000 now U.S. Pat. No. 6,433,233.

FIELD OF THE INVENTION

The present invention relates to a method of preparing pentafluoroethane, catalysts for fluorination and a preparation method thereof.

PRIOR ART

Generally, since saturated halogenated hydrocarbons containing hydrogen (hereinafter sometimes referred to as alternative flon) have an extremely low possibility of destroying the ozone layer, they have attracted much attention as an alternative to halogenated carbons without hydrogen (for example, chlorofluoroethanes: hereinafter sometimes referred to as specific flon) which have been used on the market.

In particular, pentafluoroethane is expected to satisfy a wide range of uses as a refrigerant, a foaming agent, a solvent, and a dry etchant. Further, pentafluoroethane is a useful substance because it is an inert and low-toxicity gas under normal temperatures and pressures.

In the conventional preparation methods for pentafluoroethane, it has been known that a gas phase fluorination reaction of tetrachoroethylene or halogenated hydrocarbons [$C_2HCl_xF_{(5-x)}$; wherein x is 1–5] uses a chromium oxide catalyst or an alumina catalyst carrying metals and so on.

However, it has been obvious that the conventional known reaction cannot avoid the generation of chlorofluoroethanes (specific flon) as by-products, in addition to the objective product, pentafluoroethane and halogenated hydrocarbons represented as $C_2HCl_xF_{(5-x)}$ (where x is 1–5) which can be recycled in the reaction system as the starting material.

In addition, chlorofluoroethanes [$C_2Cl_xF_{(6-x)}$; where x is 1–5] of this specific flon cannot be recycled in the reaction system as the starting material, resulting in a production loss, difficulty in separation from the objective product (pentafluoroethane) in the purification process leading to a cost increase for the purification equipment and lower purification, especially in the case of 1-chloro-1,1,2, 2,2,- pentafluoroethane (hereinafter referred to as CFC-115). Further, much expense is required for the treatment.

First, the conventional methods of preparing pentafluoroethane using a chromium oxide catalyst or an activated carbon catalyst carrying chromium or chromium oxide are described.

For example, it is disclosed in U.S. Pat. No. 3,755,477 that pentafluoroethane is produced using 2,2-dichloro-1,1, 1-trifluoroethane (hereinafter referred to as HCFC-123) as a starting material in the presence of a chromium oxide catalyst. JP Open. No. 8-38904 illustrates that pentafluoroethane is generated from perchloroethylene in the presence of a chromium oxide catalyst treated reductively. Further, in WO No. 92/19576, it is disclosed that pentafluoroethane is produced from HCFC-123 in the presence of a chromium oxide prepared from $(NH_4)_2Cr_2O_7$. It is also disclosed in EP No. 456552 that pentafluoroethane is produced using HCFC-123 as a starting material in the presence of an activated carbon catalyst carrying Cr.

However, since the conventional methods using said catalysts, such as a chromium oxide catalyst and an activated carbon catalyst carrying chromium or chromium oxide, are limited in reducing the problematic chlorofluoroethane by-products as described above, improvement in the problem of generating chlorofluoroethanes is still insufficient.

Especially in any of the said methods, it is difficult to lower the ratio of the total yield of chlorofluoroethane by-products to not more than 1% of the yield of the objective product, pentafluoroethane.

Another method of preparing pentafluoroethane is known using alumina or aluminum fluoride catalysts carrying metals.

For example, the methods of preparing pentafluoroethane are disclosed using starting materials such as perchloroethylene, 1,1,2-trichloro-2,2-difluoroethane (hereinafter referred to as HCFC-122) or HCFC-123 in the presence of the catalysts: $Cr_2O_3/AlF_3$ in EP No. 638535; Mn (or Co, Cr)/AlF$_3$ in JP Publ. No. 3–505328; Zn/alumina in WO No. 92/16482; Co/Ce/alumina in JP Open. No. 4–29940; and Cr/Ni/Al oxide catalyst in EP No. 609124.

Compared to the cases using chromium oxide catalysts, the cases using these catalyst with alumina or aluminum fluoride as a carrier lead to a low reactivity being forced to react at a high temperature. Consequently, it not only creates conditions for an increase in generation of the by-products, but also leads to increase both in equipment costs for heat of reactors and running costs. Further, the larger reactor made of a higher quality material is required resulting from the necessity for a large amount of the catalyst.

New catalysts for the preparation of pentafluoroethane are proposed in which the catalyst is a chromium catalyst such as chromium oxide or fluorinated chromium oxide which has been made to carry metals.

However, in most of these, the yield of the chlorofluoroethane by-products is not considered. In addition, they do not illustrate the preparation methods of pentafluoroethane showing a highly-active fluorination; namely, a high yield of pentafluoroethane and a controlled generation of chlorofluoroethane by-products. For example, in JP Open. No. 2-178237, pentafluoroethane is prepared by fluorination of perchloroethylene using a catalyst $Fe_2O_3$—$Cr_2O_3$ with a good yield. In JP Open. No.7-61944, pentafluoroethane is obtained by using HCFC-123 as a starting material and a catalyst In/CrO$_x$F$_y$ (the catalyst shown in the published patent gazette is specified with a composition that gives a Cr valence of +3.0) treated with hydrogen at 400° C. for 4 hr. In JP Open. No. 8-108073, preparation of pentafluoroethane is also disclosed using HCFC-123 as a starting material and a catalyst Ga/CrO$_x$F$_y$ (the catalyst shown in the published patent gazette is specified with a composition that gives a Cr valence of +3.0) treated with hydrogen at 400° C. for 4 hr. Both gazettes show the controlled effect on lowering the activity due to an increase in the reaction pressure and the long life of the catalyst.

However, none of the said examples show findings relating to the generation of chlorofluoroethane by-products.

Namely, although WO No.95/27688 discloses a method of preparing pentafluoroethane using catalysts of Zn/Cr oxides, this does not illustrate the finding relating to the total yield of chlorofluoroethane by-products. The amount of CFC-115 is shown, however, in the example using perchloroethylene as a starting material, the ratio of CFC-115 to pentafluoroethane generated is 0.59%. Further, in the example using HCFC-123 as a starting material, even the ratio of CFC-115 to the combined amount of HFC-125 with HCFC-124 already reaches 1.46%; accordingly, the reducing effect on chlorofluoroethanes is insufficient.

Further, a method of preparing pentafluoroethane from perchloroethylene using an Mg/Cr oxide catalyst is disclosed in EP No. 733611. However, large amounts of chlorofluoroethane by-product are obviously generated in all examples shown there, compared with the comparative example, and the ratio of the total amount of chlorofluoroethane generated to the amount of pentafluoroethane generated is high, and in the range of 2.9 to 7.0%.

In another fluorination reaction of 2-chloro-1,1,1-trifluoroethane (hereinafter referred to as HCFC-133a), a chromium oxide catalyst with the addition of some metals is also proposed.

For example, the fluorination reaction of HCFC-133a is disclosed in JP Open. No. 2-172933 using a catalyst comprised of halogenated compounds or oxides containing Cr and at least one element selected from a group composed of Al, Mg, Ca, Ba, Sr, Fe, Ni, Co, and Mn. The fluorination reaction of HCFC-133a is also disclosed in EP No. 546883, where the catalyst composed of a base material of an oxide of Cr mixed with Ni prepared by a hydroxide sol of $Cr^{3+}$ with $Ni^{2+}$ is used. However, this literature does not show findings relating to activity and selectivity of the generation reaction of pentafluoroethane or the yield of chlorofluoroethanes. Also, the reactivity of the generation reaction of pentafluoroethane cannot be easily predicted. Further, since the catalyst in the former is calcinated at 450° C. for 5 hr and also the catalyst in the latter is prepared through calcination at 420° C. for 4 hr, the average valence of the Cr becomes approximately +3.0. Therefore, these conditions are unsuitable to obtain an amorphous catalyst.

PURPOSE OF THE INVENTION

The present invention has been accomplished in consideration of the existing facts described above. The purpose is to provide a method of preparing pentafluoroethane using catalysts that are capable of (1) reducing the total yield of chlorofluoroethane by-products when preparing pentafluoroethane without significantly deteriorating the generation activity of the objective product, pentafluoroethane, and $C_2HCl_xF_{(5-x)}$ here x is an integer between 1 and 5), which can be recycled in the reaction system as a starting material; (2) consequently controlling production losses as well as purification equipment costs; and (3) improving the purity of the pentafluoroethane produced.

Another object of the present invention is to provide catalysts for fluorination which can be used in the preparation of pentafluoroethane described above and a preparation method thereof.

CONSTITUTION OF THE INVENTION

In order to solve said problems, the present inventors have examined improvements to chromium catalysts such as chromium oxide and fluorochromium oxide and found that chromium catalysts in an amorphous state with an average valence of the chromium not less than +3.5 but not more than +5.0 and with the addition of at least one metal element selected from a group composed of indium, gallium, cobalt, nickel, zinc and aluminum are capable of reducing the total yield of chlorofluoroethane by-products when preparing pentafluoroethane without significantly deteriorating the generating activity of pentafluoroethane and of $C_2HCl_xF_{(5-x)}$ (where X is an integer between 1 and 5), which can be recycled in the reaction system as the starting material.

Namely, as a result of an examination aiming at the relationship between the chromium valence and the reactivity in the added chromium catalyst, the present inventors have revealed that said effect is obtained using catalysts for which the average valence is about +4. This is assuming that the valence variation to be considered as one of the catalytic properties of the chromium is easy to occur. Because a valence of +6 is thermally unstable and also often shows sublimation, it has sometimes posed problems in use as a catalyst.

Further, it is proved that the average valence of chromium as an entire catalyst specified by the results of the composition analysis and determination of the magnetic susceptibility does not always have a comparatively stable integer value of +3, +4 or +6. That is because the average valence is not considered to give integer values due to mixing of chromiums of valence of +3, +4 or +6, For the above reason, the average valence of the chromium, including mainly chromium with a valence of +4, should be defined as not less than +3.5 but not more than +5 (preferably +4 to +4.5). By being not less than +3.5, the catalytic activity is improved compared with lower values, and by being not more than +5.0, the catalyst becomes highly active with a stable structure compared with higher value. Further, by adding said metals to these chromium catalysts, a highly-active catalyst which generates hardly any chlorofluoroethanes is obtained with the above effect.

Namely, the present invention relates to a method of preparing pentafluoroethane (hereinafter referred to as the present inventive method of preparing pentafluoroethane) wherein chlorine-containing carbon compounds are fluorinated under the presence of chromium catalysts that are in an amorphous state. The main component of said chromium catalysts is chromium compounds with the addition of at least one metal element selected from the group composed of indium, gallium, cobalt, nickel, zinc and aluminum. The average valence of chromium in said chromium compounds is to be not less than +3.5 but not more than +5.0.

As aforementioned, although some chromium oxide or fluorinated chromium oxide catalysts having a chromium valence of +3 with added metals are proposed, the following findings have been found through meticulously repeated studies by the present inventors:

In the presence of a chromium catalyst in an amorphous state which contains the chromium compound with the addition of at least one metal element selected from the group composed of indium, gallium, cobalt, nickel, zinc and aluminum, this compound having a valence larger than +3, in which the compound is stable, and smaller than +6, in which the compound often shows sublimation, and preferably not less than +3.5 but not more than +5.0;

by fluorinating such compounds as chlorine-containing hydrocarbons, including perchloroethylene, 1,1-dichloro-2, 2,2-trifluoroethane and 1-chloro-1,2,2, 2-tetrafluoroethane, both a highly-active pentafluoroethane generation reaction and a decrease in the ratio of the yield of chlorofluoroethane by-products to the yield of pentafluoroethane can be brought about.

In particular, said high activity leads to a decrease in both equipment costs and running costs by enabling a lower reaction temperature, decrease in the catalytic amount, and long-life catalyst. Moreover, since in practice hardly any chlorofluoroethane by-products are generated, further generation of chlorofluoroethane by-products can be controlled.

The activity in the main reaction (the generation reaction of pentafluoroethane) of the catalyst in an amorphous state with a chromium valence of +3.5 to +5 is much higher than the activity of a crystalline catalyst or a catalyst with a chromium valence of +3. This high activity, which is a characteristic of a catalyst's amorphous nature, can be fully utilized to control the amount of specific flon generated by adding metal elements. In addition, to generate the same amount of HFC-125, the high activation of the amorphous catalyst enables the lowering of the reaction temperature and, due to the effect of the added metals, results in a dramatically lower absolute amount of specific flon than if using a crystalline catalyst.

Herein, said average valence of the present invention means a chromium valence specified by composition analysis and determination of the magnetic susceptibility. The average valence of the chromium in said catalyst specified by said composition analysis is calculated from the result obtained by actually conducting a composition analysis on the said chromium catalyst. The average valence of the chromium in said catalyst specified by determination of the magnetic susceptibility is theoretically calculated from the result obtained by the change in the magnetic susceptibility of said catalyst resulting from a change in temperature. (Concrete measurement methods will be described later.)

Herein, said average valence is preferably not less than +3.6 but not more than +4.8 (furthermore preferably not less than +4.0 but not more than +4.5).

Further, said amorphous state means an amorphous state of the whole catalyst and this is the state where no diffraction peak assigned to a specific crystalline structure exists in the X-ray diffraction measurement, for example.

The fluorination reaction of the present inventive method of preparing pentafluoroethane may use HF, $F_2$ or the other fluorine-containing hydrocarbons as the fluorinating agent.

The present invention provides chromium catalysts for fluorination which can be used in the present inventive method of preparing pentafluoroethane. The main component of said chromium catalysts, which is in an amorphous state (hereinafter referred to as the present inventive catalysts), is chromium compounds with the addition of at least one metal element selected from the group composed of indium, gallium, cobalt, nickel, zinc and aluminum. The average valence of the chromium in said chromium compounds is not less than +3.5 but not more than +5.0.

The present inventive catalyst is a chromium catalyst for fluorination reaction submitted to various fluorination reactions, preferably in particular submitted to a method of preparing pentafluoroethane obtained by fluorination of ethanic and ethylenic chlorinated hydrocarbons (or chlorinated carbons).

Further, as a preparation method of the present inventive catalyst with good reproducibility, when preparing the chromium catalyst in an amorphous state for fluorination, the main component of which is chromium compounds with the addition of at least one metal element selected from the group composed of indium, gallium, cobalt, nickel, zinc and aluminum and the average valence of the chromium in said chromium compounds being not less than +3.5 but not more than +5.0;

the present invention provides a method of preparing catalysts for fluorination (hereinafter referred to as the method of preparing the present inventive catalyst) wherein the chromium catalyst in said amorphous state for fluorination is obtained by calcinating in an atmosphere of inert gas.

According to the method of preparing the present inventive catalyst, when preparing the present inventive catalyst, the chromium catalyst for fluorination which is in said amorphous state can be obtained by calcinating in an atmosphere of inert gas such as nitrogen, for example. Said calcination can be conducted at a temperature of 380° C. to 410° C. for 0.5 hr to 3.5 hr.

First, the present inventive method of preparing pentafluoroethane is illustrated.

In the present inventive method of preparing pentafluoroethane, it is preferable to fluorinate at least one of said chlorine-containing hydrocarbons selected from the group composed of perchloroethylene, 1,1-dichloro-2,2,2-trifluoroethane and 1-chloro-1,2,2,2-tetrafluoroethane by hydrogen fluoride.

Further, it is desirable that said chlorine-containing carbon compounds are any of 1,1-dichloro-2,2,2-trifluoroethane (HCFC-123) and 1-chloro-1,2,2,2-tetrafluoroethane (HCFC-124) or their mixture.

Namely, when using HCFC-123 and HCFC-124 (especially HCFC-124) as the starting material, the generation of chlorofluoroethane by-products can be controlled to an extremely small amount and simultaneously the objective pentafluoroethane can be obtained with a high yield.

Of course, perchloroethylene can be used as the starting material and in this case, it is considered that perchloroethylene is converted to pentafluoroethane through intermediates such as HCFC-123 and HCFC-124.

The present inventive method of preparing pentafluoroethane as described above is extremely effective especially in the reaction which generates chlorofluoroethane by-products. Accordingly, in the present invention, such a reaction is not limited to starting materials. However, the reaction is extremely effective in the case of fluorination by hydrogen fluoride of any of perchloroethylene, 1,1-dichloro-2,2, 2-trifluoroethane and 1-chloro-1,2,2,2-tetrafluoroethane or their mixture or a mixture of 1,1-dichloro-2,2, 2-trifluoroethane and 1-chloro-1,2,2,2-tetrafluoroethane for which the yield of pentafluoroethane is relatively high and the amount of chlorofluoroethanes generated is large. 1, 1,2-trichloro-2,2-difluoroethane (HCFC-122) and the like may be used as the said chlorine-containing carbon compounds.

The conditions of the fluorination reaction in the present inventive method of preparing pentafluoroethane can be selected according to the characteristics of each starting material.

For example, the molar ratio for the reaction of HF with the chlorine-containing carbon compounds (especially any of perchloroethylene, HCFC-123 and -124) as starting materials is usually (0.9–100): 1, and the reaction temperature is usually 150° C. to 450° C. The contact time of said catalyst with the reaction gas (value obtained by dividing the catalyst weight by the amount of reaction gas flowing per unit time) is usually 0.1 g/NmL·sec-50 g/NmL·sec. For this, preferable reaction pressure can be selected appropriately by the species of starting gas submitted to the reaction.

For example, in the fluorination reaction which generates pentafluoroethane from HCFC-123, the conversion ratio to pentafluoroethane and the yield of chlorofluoroethanes can be varied by appropriately changing the molar ratio, the reaction temperature, the contact time, and the pressure of reaction of the fluorinating agents such as HF with HCFC-123. The conversion ratio to pentafluoroethane tends to rise as the reaction temperature and the contact time increase.

Considering the cost of manufacturing equipment, the running costs for the reaction conditions and the above reaction conditions, the reaction temperature should preferably be 250° C. to 380° C. and the molar ratio of the reaction should be preferably 2 to 10. Further, the contact time should preferably be 0.2 g/NmL·sec-20 g/NmL·sec. Furthermore, the reaction pressure should preferably be near atmospheric pressure. Although the reaction can be conducted under pressures higher than atmospheric pressure, the conversion ratio to pentafluoroethane tends to lower.

According to the present inventive method of preparing pentafluoroethane, when fluorinating 1,1-dichloro-2,2,2-trifluoroethane as said chlorine-containing carbon compound under the presence of said chromium catalyst, the ratio of the total yield of chlorofluoroethane by-products to the yield of pentafluoroethane obtained can be fully controlled to be not more than 0.5%.

Further, when fluorinating 1-chloro-1,2,2,2-tetrafluoroethane as said chlorine-containing carbon compound, the ratio of the total yield of chlorofluoroethane by-products to the yield of pentafluoroethane obtained can be fully controlled to not more than 0.3%.

Thus, according to the present inventive method of preparing pentafluoroethane, the efficient preparation of pentafluoroethane can be conducted without significantly deteriorating the yield of pentafluoroethane and generation activity of $C_2HCl_xF_{(5-x)}$ (where x is an integer between 1 and 5), which can be recycled, and the ratio of the total yield of chlorofluoroethane by-products to the yield of pentafluoroethane obtained can be controlled to not more than 0.5% or 0.3%, and in addition, the total yield of chlorofluoroethane which can not be recycled to the reaction system as a starting material is lowered, and the generation of CFC-115 which is difficult to separate from pentafluoroethane can be controlled.

In the the present inventive method of preparing pentafluoroethane, said chromium compounds may be at least one species selected from the group composed of chromium oxide, chromium fluoride, fluorochromium oxide and chlorofluorochromium oxide. Namely, the catalyst used in the present inventive method of preparing pentafluoroethane may be mixtures of such various forms, for example, fluorochromium oxide and the like including chromium of different valences.

Prior fluorination is preferable before said chromium catalyst is submitted to the fluorination reaction of said chlorine-containing carbon compounds. For example, the fluorination can be conducted by setting said catalyst at a prescribed temperature and for a prescribed time in a mixture of HF gas and $N_2$ gas.

Herein, said chromium catalyst such that the specific surface area becomes 25–130 m$^2$/g after said fluorination can be used. Namely, chromium oxide including amorphous Cr of high valence with added metals is prepared by the above method, thereafter the catalyst of 25–130 m$^2$/g is spontaneously obtained by performing HF gas treatment at 100 to 460° C., preferably at 150 to 400° C. This reaction is conducted using HF diluted with nitrogen gas (HF: 5 to 20%) at a low temperature (150 to 250° C.) in the beginning of the HF treatment which is an extremely large exothermic reaction; thereafter a rise in the temperature or increase in the HF concentration is desirable.

The amorphous state of said chromium catalyst can be made by calcinating said chromium catalyst conducted in an atmosphere of inert gas.

The amorphous chromium catalyst having the valence described above can be formed by said calcination within the above temperature and time. Especially, said calcination is preferably conducted within the temperature and time ranges of 380 to 410° C. and 0.5 to 3.5 hr, respectively. Moreover, in the present inventive method of preparing pentafluoroethane, addition methods of said metal elements to said chromiumcatalyst are not limited. For example, after immersing chromium hydroxide in an aqueous solution of said metal elements followed by drying, said calcination may be conducted (impregnation method or immersion method: refer to FIG. 1). Or after obtaining chromium hydroxide containing said metal elements by coprecipitation from an aqueous solution dissolving said metal elements and chromium followed by drying, said calcination may be conducted (coprecipitation method: refer to FIG. 2).

Namely, for example, there is the impregnation method wherein chromium catalysts or chromium hydroxide, which is the precursor of the chromium catalyst, are immersed in an aqueous solution of said metal salts followed by drying and calcination, and there is the coprecipitation method wherein a precipitant such as aqueous ammonia is added to a mixed aqueous solution comprising an aqueous solution of metal salts of said metal elements and an aqueous solution of chromium salt to give chromium hydroxide containing said metal elements and is followed by calcination. Using these methods, at least one metal element selected from the group composed of In, Ga, Co, Ni, Zn and Al is added to a chromium compound.

While the added amount of said metal element to the chromium catalyst such as chromium oxide may not be too small to obtain the present inventive effect, it may not be enough to significantly inhibit the reactivity of the chromium catalyst. Namely, the ratio of number of atom to Cr in the catalyst is desirable within the range of 0.001 to 0.5, and preferably 0.005 to 0.1 (the method of preparing the present inventive catalyst is the same).

Thus, when fluorinating said catalyst by HF and the like in order to stabilize the initial activity of said catalyst and to dehydrate, addition of said metal elements is possible after said fluorination treatment; however, it is desirable to be conducted before fluorination treatment.

In the present inventive method of preparing pentafluoroethane, the addition or carrying of an element having an improving effect on the reactivity or selectivity to said chromium catalyst except chromium, indium, gallium, cobalt, nickel, zinc, aluminum, oxygen, chlorine and fluorine, is desirable. Said element may be at least one element selected from the group composed of cadmium, magnesium and titanium.

When fluorinating said chlorine-containing carbon compounds using hydrogen fluoride, a part or all of the generating products can be returned to the reaction system or can be led to another reaction system in which fluorination is conducted by hydrogen fluoride using catalysts as claimed in claim 1. Further, separating the mixture containing pentafluoroethane and hydrogen chloride from said products, the residual products may be returned to said reaction system or may be led to said another reaction system.

Such processes make it possible to prepare pentafluoroethane more efficiently.

Next, the present inventive catalyst is illustrated.

In the present inventive catalysts, said chromium compounds may be at least one species selected from the group composed of chromium oxide, chromium fluoride, fluorochromium oxide and chlorofluorochromium oxide. Namely, if the chromium valence is within the range of said valence number, it may be of said various forms.

The present inventive catalyst is desirably fluorinated. Especially, the specific surface area after said fluorination is preferably within 25–130 m$^2$/g.

In the present inventive catalysts, the addition of an element having an improving effect on reactivity or selectivity except chromium, indium, gallium, cobalt, nickel, zinc, aluminum, oxygen, chlorine or fluorine is desirable. Said element may be at least one element selected from the group composed of cadmium, magnesium and titanium.

Next, the method of preparing the present inventive catalyst is illustrated.

By treating chromium hydroxide obtained from a preparation method described later at high temperature in an inert atmosphere, dehydration as well as generation of chromium oxide proceed, and simultaneously, the surface area increases. These phenomena proceed by calcination even under the conditions of a comparatively lower temperature of between 300° C. and 370° C., or a short time of 0.4 hr and a sufficiently large surface area is obtained. However, many hydroxyl groups (OH⁻) in the catalyst remain in this calcination condition and thus the chromium valence in the catalyst obtained becomes a value below +3.5. Inversely, in calcination conditions of above 410° C. or beyond 3.5 hr, the valence of the chromium ion transfers from stable +4 to +3. On the crystal structure of chromium oxide, the catalyst also transfers from an amorphous to a stable $Cr_2O_3$ (Cr +3 valence) crystalline structure and in addition the average valence of chromium becomes a value below +3.5.

From the above examination results, in order to obtain a catalyst where the average valence of chromium in the amorphous state shows not less than +3.5 but not more than +5.0 by calcinating chromium hydroxide obtained from the preparation method illustrated in the present application, calcination at 380° C. to 410° C., especially 400° C. and for 0.5 to 3.5 hr, preferably 2 hr in an inert atmosphere is suitable.

After immersing powdered chromium hydroxide in an aqueous solution of said metal elements followed by drying, said calcination can be conducted (impregnation method or immersion method: refer to FIG. 1). Or after obtaining chromium hydroxide containing said metal elements by coprecipitation from an aqueous solution dissolving said metal elements and chromium followed by drying, said calcination may be conducted (coprecipitation method: refer to FIG. 2).

Said chromium compounds in the method of preparing the present inventive catalysts may be at least one species selected from the group composed of chromium oxide, chromium fluoride, fluorochromium oxide and chlorofluorochromium oxide.

In the method of preparing the present inventive catalyst, fluorination after said calcination of said catalyst is desirable. The said fluorination can be conducted for controlling the specific surface area of said catalyst for fluorination to within 25–130 m²/g.

Further, in said catalyst for fluorination in the present inventive method, addition of an element having an improving effect on reactivity or selectivity except chromium, indium, gallium, cobalt, nickel, zinc, aluminum, oxygen, chlorine and fluorine is desirable.

Said element may be at least one element selected from the group composed of cadmium, magnesium and titanium.

In the method of preparing the present inventive catalyst, the average valence number of the chromium in said catalyst is not less than +3.5 but not more than +5.0 and the catalyst is amorphous. Such a catalyst for fluorination is prepared by the following method, for example.

First, precipitate of chromium hydroxide is obtained by mixing an aqueous solution of chromium salt (for example, chromium nitrate, chromium chloride, chrome alum and chromium sulfate) and aqueous ammonia.

Next, for example, precipitate of chromium hydroxide is obtained by dropping 10% aqueous ammonia equivalent to about 1.2 times into a 5.7% aqueous solution of chromium nitrate. In this process, although the property of chromium hydroxide can be controlled through the reaction rate of the precipitation reaction, the reaction rate is desirably rapid to a considerable extent. This reaction rate is controlled by the temperature of the reaction solution, the mixing method for the aqueous ammonia (mixing rate) and the stirring conditions.

Subsequently, this precipitate is filtered, washed and dried. This drying is desirably performed at 70° C. to 140° C. in air, especially at around 120° C. for 1 hr to 50 hr, especially for around 12 hr, for example. The material obtained in this step is chromium hydroxide.

Next, after this chromium hydroxide is immersed, for example, in an aqueous solution of indiumnitrate (for example, in order to control the atomic ratio of indium in the aqueous solution of indium nitrate to chromium in this chromium hydroxide to be about 1:0.03, the concentration of said aqueous solution is adjusted) for about 12 hr, chromium hydroxide with added indium is obtained by drying at 120° C. for 12 hr, for example.

Next, to make a pellet-shaped catalyst, after grinding the chromium hydroxide with added indium, the shape is molded into a pellet by a tableting machine. The pellet may be cylindrical of 3 mm in diameter and about 3 mm in height. Considering the pressure loss and the diffusion of the gas flow, said pellet is desirably molded in a hollow cylindrical form.

By calcinating the molded catalyst in an atmosphere of an inert gas such as nitrogen, the average valence number of the chromium is not less than +3.5 but not more than +5.0 and the amorphous chromium oxide is prepared.

The calcination temperature is preferably not less than 380° C. However, $Cr_2O_3$ (chromium valence is +3) composition is formed if too high; therefore, it is desirable to set the higher temperature within the range that is capable of avoiding it. Accordingly, this calcination is carried out, for example, at 380° C. to 410° C., especially around 400° C. for 0.5 hr to 3.5 hr, especially for around 2 hr. As described above, if this calcination time is longer than the above range, $Cr_2O_3$ is generated and the chromium catalyst having a high average valence number cannot be obtained, while if too short, the number of the remaining hydroxyl group in the catalyst tends to become too high.

Next, fluorination treatment of the catalyst can be carried out with CFCs, HCFCs, HF or $F_2$. If the fluorination treatment is not conducted, the generation reaction of objective pentafluoroethane is severely inhibited and generation of by-products is sometimes accelerated since fluorination of the catalyst proceeds during the generation reaction of pentafluoroethane.

Especially in the case of fluorination treatment with HF, the higher the temperature and the pressure are, the larger the rate of progress is. The temperature at which the generating water is not condensed in the process and at which the catalyst is not crystallized by the reaction heat may be maintained as the upper limit. For example, the temperature when fluorinating may be within the range of 100° C. to 460° C.

Herein, the specific surface area of the catalyst decreases in the range of 25 m²/g to 130 m²/g by this fluorination treatment.

Except for the above method, preparation of the chromium catalyst is possible wherein the average valence number of chromium in the catalyst is within not less than +3.5 but not more than +5.0 and the catalyst is in the amorphous state. However, in order to obtain the present inventive catalyst, the various conditions for obtaining chromium hydroxide by precipitation reaction (neutralization reaction) and calcination condition of chromium hydroxide and so on in the above method of preparing the catalyst are especially significant.

Herein, as for an example of another preparation method except the above preparation examples of the catalyst, there are coprecipitation methods for obtaining the precipitate of chromium hydroxide by mixing an aqueous solution of indium nitrate with an aqueous solution of chromium nitrate instead of impregnating an aqueous solution of indium nitrate into chromium hydroxide Industrial Application According to the present inventive method of preparing pentafluoroethane, since (1) chlorine-containing carbon compounds are fluorinated in the presence of chromium catalysts that are in an amorphous state; (2) the main component of said chromium catalysts is a chromium compound with the addition of at least one metal element selected from the group composed of indium, gallium, cobalt, nickel, zinc and aluminum; and (3) the average valence of chromium in said chromium compound is not less than +3.5 but not more than +5.0, it is possible to decrease the total yield of chlorofluoroethane by-products when preparing pentafluoroethane without significantly deteriorating the generation activity of th e pentafluoroethane and $C_2HCl_xF_{(5-x)}$ (where x is an integer between 1 and 5), which can be recycled in the reaction system as a starting material.

The present inventive catalysts, which are in an amorphous state and wherein the main component is chromium compounds with the addition of at least one metal element selected from the group composed of indium, gallium, cobalt, nickel, zinc and aluminum and the average valence of chromium in said chromium compounds is not less than +3.5 but not more than +5.0, are useful as catalysts for fluorination in various fluorination reactions and can be submitted especially to the present inventive method of preparing pentafluoroethane.

According to the method of preparing the present inventive catalyst, when preparing the chromium catalyst in an amorphous state for fluorination wherein chromium compounds with the addition of at least one metal element selected from the group composed of indium, gallium, cobalt, nickel, zinc and aluminum are contained as the main component and the average valence of the chromium in said chromium compounds is not less than +3.5 but not more than +5.0, since the chromium catalyst in said amorphous state for fluorination is obtained by calcination in an atmosphere of inert gas, the chromium catalyst in said amorphous state for fluorination can be prepared with good reproducibility.

BRIEF DESCRIPTION OF THE DRAWINGS

FIG. 1 is a flowchart showing the catalyst preparation example relating to an Example of the present invention.

FIG. 3 is a flowchart showing the catalyst preparation example relating to a Comparative Example.

FIG. 4 is a graph showing the result of X-ray diffraction measurement of Catalyst 1.

FIG. 5 is a graph showing the result of X-ray diffraction measurement of Catalyst 2.

FIG. 6 is a graph showing the result of X-ray diffraction measurement of Comparative Catalyst 1.

DESCRIPTION OF THE MARKS

Figure 2:
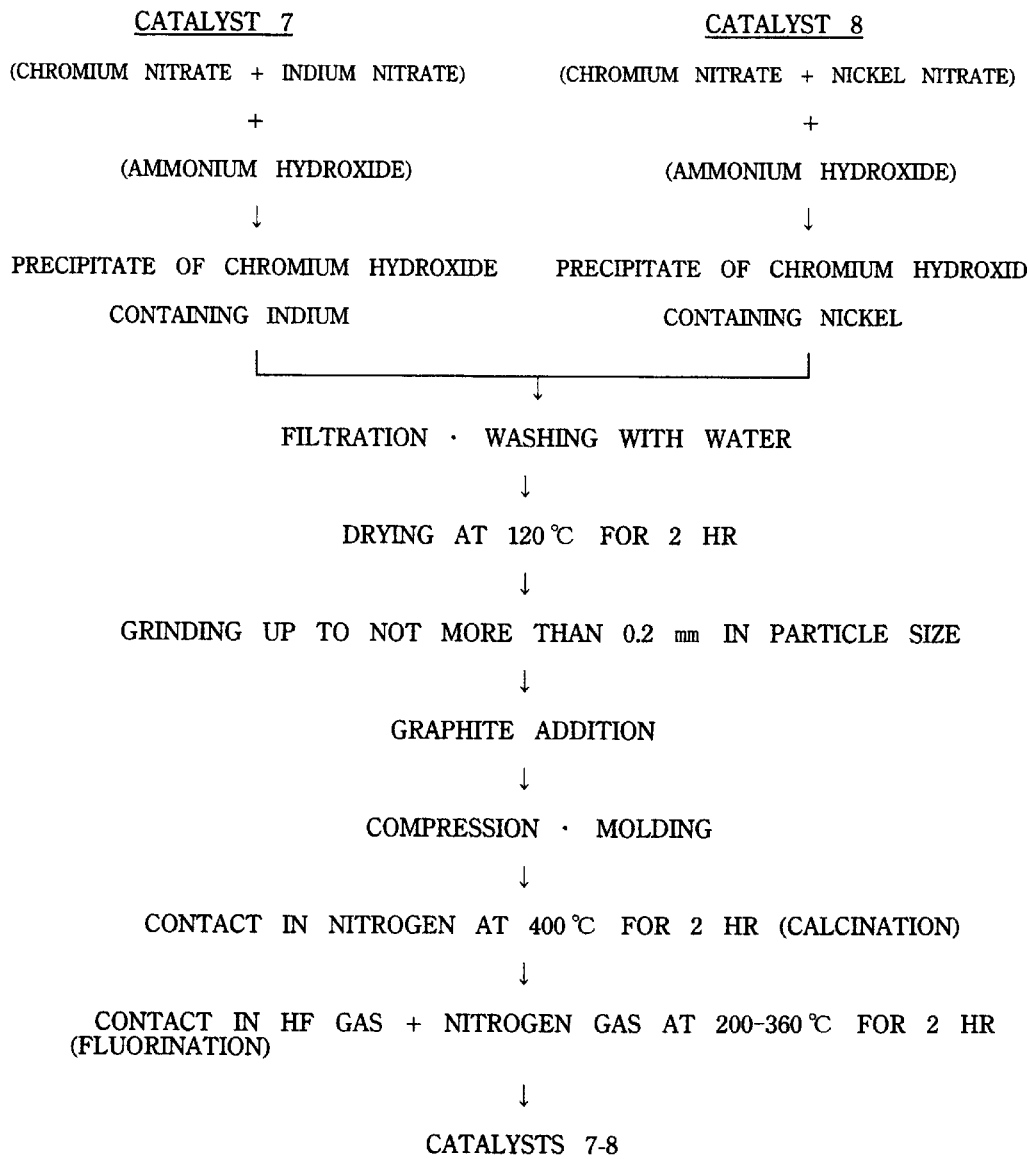
FIG. 2 is a flowchart showing the catalyst preparation example relating to another Example of the present invention.

1—Reactor
2, 3—Material containers
4—Partial condenser (heat exchanger)
5, 7, 8, 9, 11,13, 14, 15—Pipes
6—Separating tank
10—Distillation column
12—Condenser

EXAMPLE

The following Examples are given to further illustrate the present invention. However, it should be understood that the present invention is not limited by these examples.

Catalyst Preparation

First, the catalysts for fluorination (catalysts 1–8) based on the present Example and the catalysts for fluorination (comparative catalysts 1–3) for comparison were prepared.

Catalysts 1–6 (Example)

Catalysts 1–6 were prepared according to the flowchart shown in FIG. 1.

First, 1.14 kg of 10% ammonium hydroxide was dropped into 7.65 kg of 5.7% aqueous chromium nitrate solution while stirring, and the resulting precipitate of chromium hydroxide was obtained. Next, after filtrating this followed by washing with pure water, the solid chromium hydroxide obtained by drying a part of the filtrate in air at 120° C. for 12 hr was ground up to not more than 0.2 mm in particle size, thus obtaining powdered chromium hydroxide.

Next, 50 g of powdered chromium hydroxide obtained was immersed in an aqueous solution of dissolving reagents shown in the following Table 1 in 30 mL water, then allowed to stand for 12 hr, and dried to remove the water again.

Subsequently, after grinding this again, a mixed powder with 2 wt % graphite added was molded under compression into a cylindrical shape 3 mm in diameter and 3 mm in height using a commercially-available tableting machine. These were charged into a reaction tube made of Hastelloy C with an inside diameter of 20 mm and then calcinated by heating at 400° C. for 2 hr in a nitrogen gas flow. The following catalysts were obtained by fluorinating further in contact with a mixed gas of hydrogen fluoride and nitrogen at 200° C. to 360° C. for 2 hr:

Catalyst 1; fluorochromium oxide containing indium,
Catalyst 2; fluorochromium oxide containing gallium,
Catalyst 3; fluorochromium oxide containing cobalt,
Catalyst 4; fluorochromium oxide containing nickel,
Catalyst 5; fluorochromium oxide containing zinc, and
Catalyst 6; fluorochromium oxide containing aluminum.

TABLE 1

| Catalyst | Reagent | Used Amount |
|---|---|---|
| 1 | $In(NO_3)_3 \cdot 3H_2O$ | 5.16 g |
| 2 | $Ga(NO_3)_3 \cdot 8H_2O$ | 5.82 g |
| 3 | $Co(NO_3)_2 \cdot 6H_2O$ | 4.25 g |
| 4 | $Ni(NO_3)_2 \cdot 6H_2O$ | 4.23 g |
| 5 | $Zn(NO_3)_2 \cdot 6H_2O$ | 4.34 g |
| 6 | $Al(NO_3)_3 \cdot 9H_2O$ | 5.48 g |

In catalysts 1 to 6 of the present Example obtained in the above examples of catalyst preparation, the following Table 2 shows the results in terms of the composition analysis before fluorination and the valence number of the Cr calculated by that; the number valence of the Cr specified by determining the magnetic susceptibility; an X-ray diffraction measurement (XRD); and a specific surface area measurement (SSA).

Herein, the average valence number specified by the composition analysis was measured as follows.

First, the chromium was oxidized up to a valence of 6 using an alkali fusion method, and the catalyst was dissolved in an aqueous solution. Next, the chromium was quantitated by a permanganate method, which is part of an oxidation reduction titration. Determination of the hydrogen was conducted using a CHN analytical instrument (determination by thoroughly oxidizing hydrogen to $H_2O$). From the results of the quantities of chromium and hydrogen obtained, the amount of oxygen in the remaining element was calculated. Determination of $H_2O$ adsorbed in the catalyst as well as the above elemental analysis is also conducted using a differential thermal balance (the weight reduction accompanying the endothermic near 100° C. is defined as the adsorbed water amount). From the results of the elemental analysis and measurement of the differential thermal balance, the composition of the catalyst is spontaneously specified as the for m of $CrO_x \cdot (OH)_y \cdot ZH_2O$.

Next, since the valence of oxygen (O), the hydroxyl group (OH) and water ($H_2O$) are -2, -1 and 0, respectively, the valence of the remaining Cr was derived by the following equation using the results of the composition analyses:

$$Cr\ valence = -(-2 \times x - 1 \times y) - n \times m$$

(wherein n is the valence of an added metal element such as In as described above, and m is the ratio of the number of atom of the metal element added to the Cr).

The average valence number specified by measurement of the magnetic susceptibility was measured as follows.

It is generally known that the valence of a magnetic ion of a paramagnetic substance can be theoretically specified by determining the magnetic susceptibility curve (change in the magnetic susceptibility brought about by change in the temperature). Namely, the valence of Cr is specified by comparing the effective Bohr magneton number inherent to the chromium ion of each valence calculated theoretically from a number of unpaired electrons in the 3d orbital, with the effective Bohr magneton number obtained from the result of the magnetic susceptibility measurement.

First, the change in the magnetic susceptibility of the catalyst brought about by a change in the temperature was measured by using a magnetic balance. The Curie constant represented by the following equation was calculated from the result:

$$X = C/T\ (X: \text{magnetic susceptibility},\ C: \text{Curie constant},\ T: \text{temperature } [K])$$

Next, the effective Bohr magneton number was calculated by substituting the obtained value of C in the following relative Equation (A).

$$\text{Effective Bohr magneton number } \mu = \sqrt{(C/0.125)} \quad (A)$$

On the other hand, it is known that the effective Bohr magneton number of the chromium ion can be theoretically obtained from the overall spin angular momentum determined by the number of electrons in the 3d orbital of the ion. The values are shown in the following Table a.

TABLE a

| Chromium Valence | +6 | +5 | +4 | +3 | +2 |
|---|---|---|---|---|---|
| $\mu$ | 0.00 | 1.73 | 2.83 | 3.87 | 4.90 |

And based on the correlation of $\mu$ in Table a with the chromium valence, the average valence number of the chromium in the catalyst was specified from the values obtained from said Equation (A). For example, if $\mu$ is 2.72, chromium valence=+4.1 is calculated by solving the following Equations 1 and 2:

$$2.72 = 1.73x + 2.83\ (1-x) \quad \text{Equation 1 and}$$

$$\text{chromium valence} = +5x + 4\ (1-x) \quad \text{Equation 2.}$$

TABLE 2

|  | Catalyst 1 | Catalyst 2 | Catalyst 3 | Catalyst 4 | Catalyst 5 | Catalyst 6 |
|---|---|---|---|---|---|---|
| Added Metal M | In | Ga | Co | Ni | Zn | Al |
| Composition (Molar Ratio) |  |  |  |  |  |  |
| Metal (m) | 0.03 | 0.03 | 0.03 | 0.03 | 0.03 | 0.03 |
| Chromium | 1 | 1 | 1 | 1 | 1 | 1 |
| Oxygen (x) | 2.15 | 2.15 | 2.13 | 2.13 | 2.16 | 2.14 |
| OH (y) | 0.05 | 0.03 | 0.01 | 0.02 | 0.01 | 0.04 |
| $H_2O$ (z) | 0.22 | 0.21 | 0.25 | 0.22 | 0.23 | 0.28 |
| Valence |  |  |  |  |  |  |
| Composition Analysis Measurement of | +4.26 | +4.24 | +4.21 | +4.22 | +4.27 | +4.23 |

TABLE 2-continued

|  | Catalyst 1 | Catalyst 2 | Catalyst 3 | Catalyst 4 | Catalyst 5 | Catalyst 6 |
|---|---|---|---|---|---|---|
| Magnetic Susceptibility | +4.3 | +4.2 | +4.1 | +4.1 | +4.3 | +4.2 |
| Result of X-ray Diffraction | Amorphous | Amorphous | Amorphous | Amorphous | Amorphous | Amorphous |
| Specific Surface Area (m$^2$/g) | 88.0 | 92.5 | 90.0 | 93.1 | 91.8 | 89.4 |

Where "valence" is the average valence of the chromium in each catalyst before fluorination which is derived from the catalyst composition $M_m CrO_x(OH)_y zH_2O$. Here, the specific surface area is the value after fluorination.

Catalyst 7 (Example)

Catalyst 7 was prepared according to the flowchart shown in FIG. 2.

First, a mixed solution of 7.65 kg of 5.7% aqueous chromium hydroxide solution with 330 g of 10.0% aqueous indium nitrate solution was prepared. Into this mixed solution was dropped 1.21 kg of 10% ammonium hydroxide while stirring, and the resulting precipitate of chromium hydroxide with added indium was obtained.

Next, after filtrating this followed by washing with pure water, the solid chromium hydroxide obtained by drying a part of the filtrate in air at 120° C. for 12 hr was ground up to not more than 0.2 mm in particle size, thus obtaining powdered chromium hydroxide containing indium.

Subsequently, a mixed powder with 2 wt % graphite added was molded under compression into a cylindrical shape 3 mm in diameter and 3 mm in height using a commercially-available tableting machine. These were charged into a reaction tube made of Hastelloy C with an inside diameter of 20 mm and then calcinated by heating at 400° C. for 2 hr in a nitrogen gas flow. Further, fluorochromium oxide containing indium as catalyst 7 was obtained by fluorination in contact with a mixed gas of hydrogen fluoride and nitrogen at 200° C. to 360° C. for 2 hr.

As for the valence number of the Cr in the catalyst obtained, the value by composition analysis was +4.27 and the value determined from the magnetic susceptibility was +4.3. In addition, this catalyst was confirmed to be amorphous from the XRD measurement. The SSA of this catalyst 7 was 105.2 m$^2$/g.

Catalyst 8 (Example)

Catalyst 8 was obtained according to the flowchart shown in FIG. 2.

Except for using 200 g of 10.0% aqueous nickel nitrate solution instead of 330 g of 10.0% aqueous indium nitrate solution, fluorochromium oxide containing nickel was obtained as catalyst 8 by a preparation similar to the catalyst preparation of Example 7.

As for the valence number of the Cr in the catalyst obtained, the value by composition analysis was +4.23 and the value determined from the magnetic susceptibility was +4.2. In addition, this catalyst was confirmed to be amorphous from the XRD measurement. The SSA of this catalyst 8 was 108.1 m$^2$/g.

Comparative Catalyst 1

Comparative catalyst 1 was obtained according to the flowchart shown in FIG. 3.

First, 1.14 kg of 10% ammonium hydroxide was dropped into 7.65 kg of 5.7% aqueous chromium nitrate solution while stirring, and the resulting precipitate of chromium hydroxide was obtained. Next, after filtrating this followed by washing with pure water, the solid chromium hydroxide obtained by drying a part of the filtrate in air at 120° C. for 12 hr was ground up to not more than 0.2 mm in particle size, thus obtaining powdered chromium hydroxide.

Subsequently, a mixed powder with 2 wt % graphite added was molded under compression into a cylindrical shape 3 mm in diameter and 3 mm in height using a commercially-available tableting machine. These were charged into a reaction tube made from Hastelloy C with an inside diameter of 20 mm and then calcinated by heating at 400° C. for 2 hr in a nitrogen gas flow. Further, comparative catalyst 1 comprising fluorochromium oxide was prepared by fluorination in contact with a mixed gas of hydrogen fluoride and nitrogen at 200° C. to 360° C. for 2 hr.

As for the valence number of the Cr in the catalyst obtained, the value by composition analysis was +4.18 and the value determined from the magnetic susceptibility was +4.2. In addition, this catalyst was confirmed to be amorphous from the XRD measurement. The SSA of this comparative catalyst was 111.3 m$^2$/g.

Comparative Catalyst 2

Comparative catalyst 2 was obtained according to the flowchart shown in FIG. 3.

First, 1.14 kg of 10% ammonium hydroxide was dropped into 7.65 kg of 5.7% aqueous chromium nitrate solution while stirring, and the resulting precipitate of chromium hydroxide was obtained. Next, after filtrating this followed by washing with pure water, the solid chromium hydroxide obtained by drying a part of the filtrate in air at 120° C. for 12 hr was ground up to not more than 0.2 mm in particle size, thus obtaining powdered chromium hydroxide.

This was charged into a reaction tube made from Hastelloy C with an inside diameter of 20mm, and the first calcination was conducted by raising the temperature from room temperature up to 550° C. and by maintaining the temperature not below 550° C. for 2 hr in a nitrogen gas flow. Thereafter, the green-colored $Cr_2O_3$ powder was obtained on lowering the temperature. Subsequently, a mixed powder with 2 wt % graphite added was molded under compression into a cylindrical shape 3 mm in diameter and 3 mm in height using a commercially-available tableting machine. These were charged into a reaction tube made from Hastelloy C, 20 mm in inside diameter, then the second calcination was conducted by heating at 400° C. for 2 hr in a nitrogen gas flow. Further, the comparative catalyst 2 comprising fluorochromium oxide was prepared by fluorination in contact with a mixed gas of hydrogen fluoride and nitrogen at 200° C. to 360° C. for 2 hr.

As for the valence number of the Cr in the catalyst obtained, the value by composition analysis was +2.95 and the value determined from the magnetic susceptibility was +3.02. In addition, this catalyst was confirmed to show crystallinity from the result that all diffraction peaks obtained by the XRD measurement are assigned on the basis of the crystal structure of $Cr_2O_3$. The SSA of this comparative catalyst 2 was 10.4 $m^2/g$.

Comparative Catalyst 3

Comparative catalyst 3 was obtained according to the flowchart shown in FIG. 3.

First, 1.14 kg of 10% ammonium hydroxide was dropped into 7.65 kg of 5.7% aqueous chromium nitrate solution while stirring, and the resulting precipitate of chromium hydroxide was obtained. Next, after filtrating this followed by washing with pure water, the solid chromium hydroxide obtained by drying a part of the filtrate in air at 120° C. for 12 hr was ground up to not more than 0.2 mm in particle size, thus obtaining powdered chromium hydroxide.

This was charged into a reaction tube made from Hastelloy C with an inside diameter of 20 mm, and the first calcination was conducted by raising the temperature from room temperature up to 550° C. and by maintaining the temperature at not less than 550° C. for 2 hr in a nitrogen gas flow. Thereafter, the green-colored $Cr_2O_3$ powder was obtained on lowering the temperature.

Next, 45.2 g of this powder was immersed in a 30 mL aqueous solution of 5.16g of $In(NO_3)_3 \cdot 8H_2O$, then allowed to stand for 12 hr, and dried to remove the water again.

Subsequently, after grinding this again, a mixed powder with 2 wt % graphite added was molded under compression into a cylindrical shape 3 mm in diameter and 3 mm in height using a commercially-available tableting machine. These were charged into a reaction tube made from Hastelloy C, 20 mm in inside diameter, and the second calcination was conducted by heating at 400° C. for 2 hr in a nitrogen gas flow. Further, comparative catalyst 3 comprising chromium hydroxide containing indium was prepared by fluorination in contact with a mixed gas of hydrogen fluoride and nitrogen at 200° C. to 360° C. for 2 hr:

As for the valence number of Cr in the catalyst obtained, the value by composition analysis was +2.97 and the value determined from the magnetic susceptibility was +3.04. In addition, this catalyst was confirmed to show crystallinity from the result that all diffraction peaks obtained by the XRD measurement are assigned on the basis of the crystal structure of $Cr_2O_3$. The SSA of this comparative catalyst 3 was 9.5 $m^2/g$.

Next, catalysts 1 to 8 and comparative catalysts 1 to 3 obtained by the above methods were powdered by grinding in an agate mortar, then the crystallinity and crystalline structure of each catalyst were investigated by the X-ray diffraction method under the following measurement conditions, and the measurement results are shown in the following Table A:

Diffractometer: Rigaku Denki Co., Ltd., RAD-RA type diffractometer (XRD),

X-ray: CuKα-ray, and

Output power: 40 kV×100 mA.

TABLE A

Figure 7:
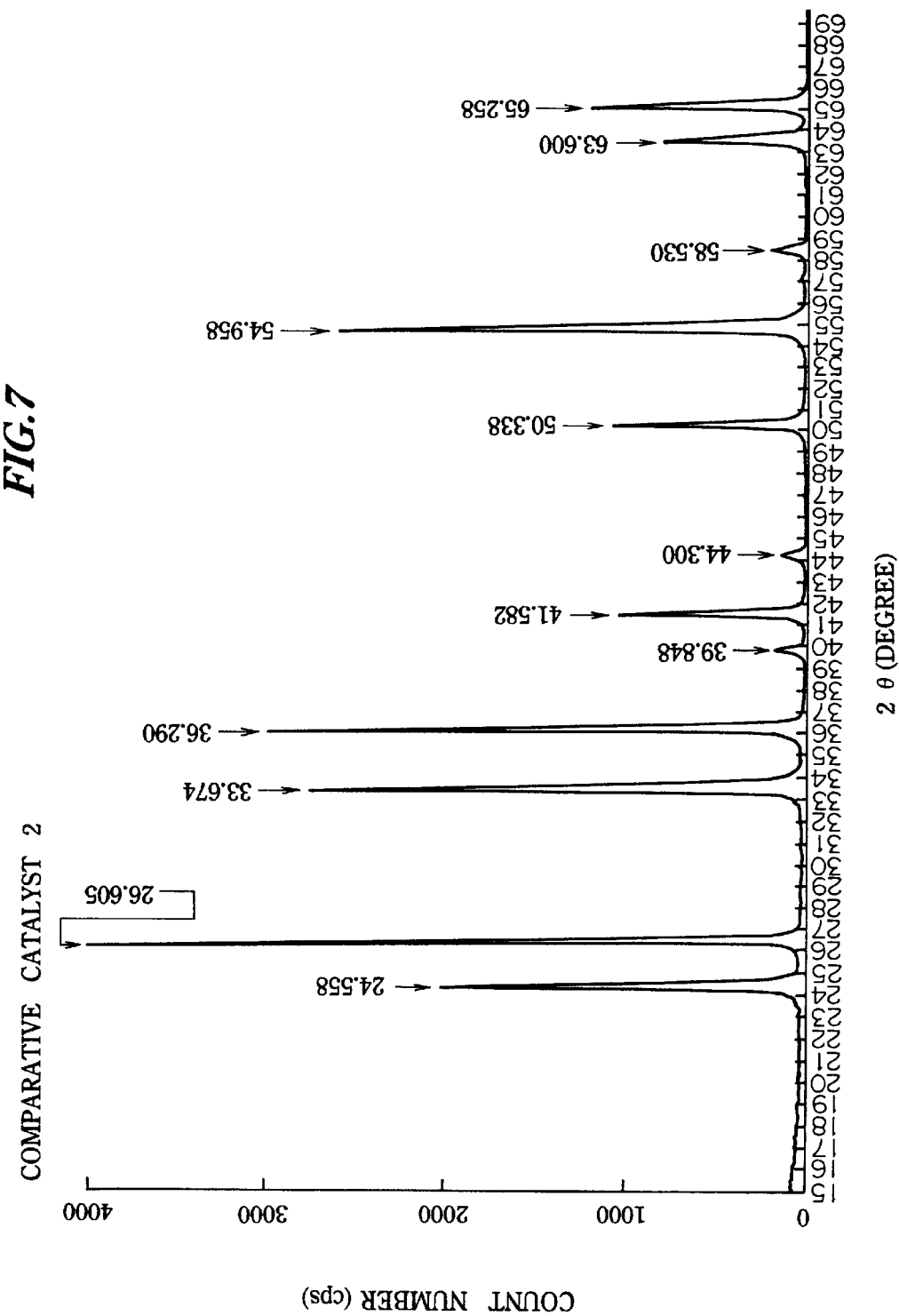
FIG. 7 is a graph showing the result of X-ray diffraction measurement of Comparative Catalyst 2.
Figure 8:
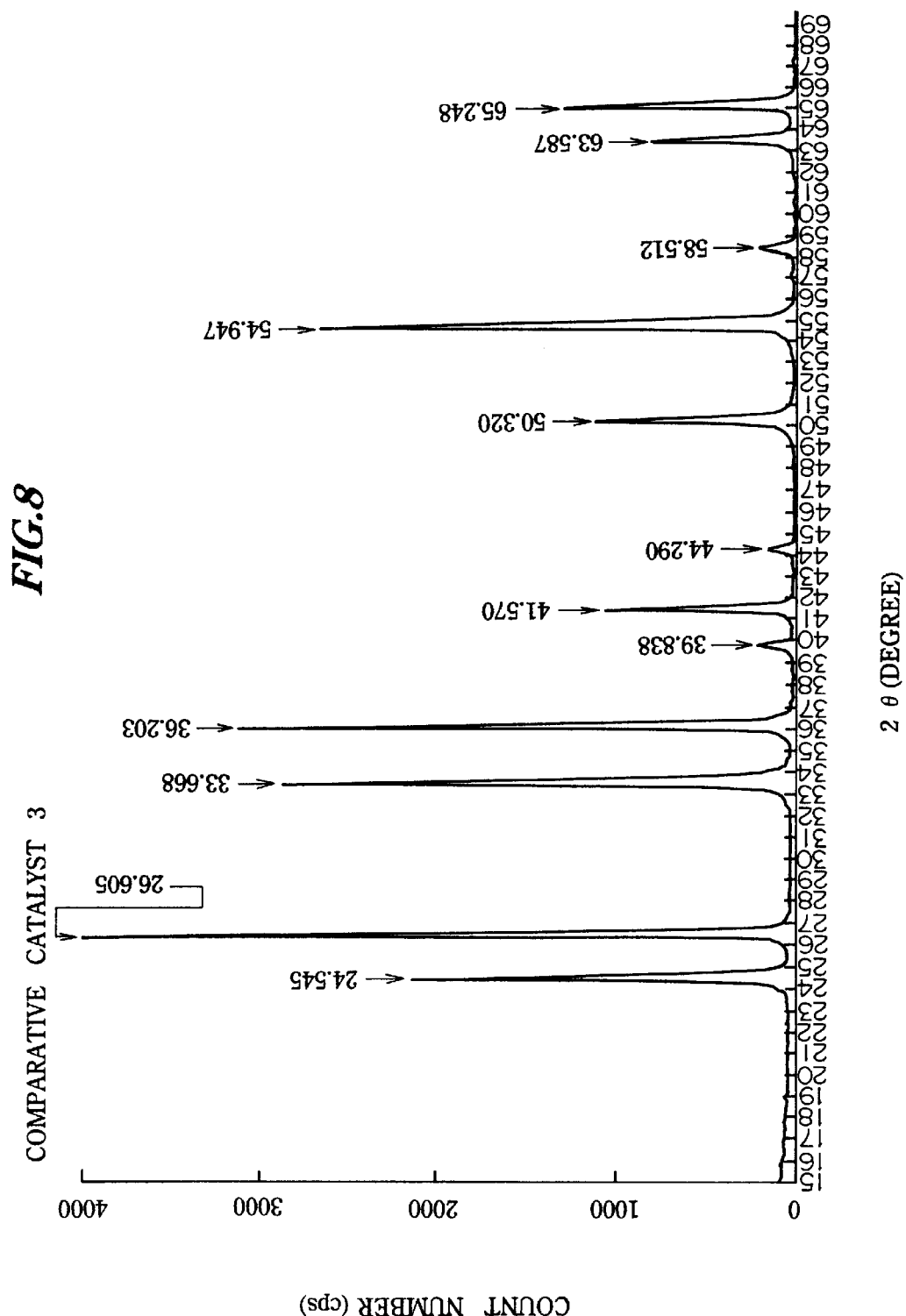
FIG. 8 is a graph showing the result of X-ray diffraction measurement of Comparative Catalyst 3.

| Catalyst | Result of XRD | Crystallinity and Crystal Structure |
| --- | --- | --- |
| Catalyst 1 | FIG. 4 | Amorphous [two diffraction peaks are observed, but assigned to carbon (graphite)] |
| Catalyst 2 | FIG. 5 | Amorphous [two diffraction peaks are observed, but assigned to carbon (graphite)] |
| Catalyst 3 | | Amorphous [no illustration: two diffraction peaks are observed, but assigned to carbon (graphite)] |
| Catalyst 4 | | Amorphous [no illustration: two diffraction peaks are observed, but assigned to carbon (graphite)] |
| Catalyst 5 | | Amorphous [no illustration: two diffraction peaks are observed, but assigned to carbon (graphite)] |
| Catalyst 6 | | Amorphous [no illustration: two diffraction peaks are observed, but assigned to carbon (graphite)] |
| Catalyst 7 | | Amorphous (no illustration: two diffraction peaks are observed, but assigned to carbon (graphite)] |
| Catalyst 8 | | Amorphous (no illustration: two diffraction peaks are observed, but assigned to carbon (graphite)] |
| Comparative Catalyst 1 | FIG. 6 | Amorphous [two diffraction peaks are assigned to carbon (graphite)] |
| Comparative Catalyst 2 | FIG. 7 | $Cr_2O_3$ (all peaks are assigned to $Cr_2O_3$ except diffraction peaks of carbon) |
| Comparative Catalyst 3 | FIG. 8 | $Cr_2O_3$ (all peaks are assigned to $Cr_2O_3$ except diffraction peaks of carbon) |

The abscissas of FIG. 4 to FIG. 8 show the incident angle 2θ of the X-rays and the vertical axes show the count rate (cps: counts per second). The diffraction peaks which the incident angle 2θ of the X-rays was revealed both at 26° to 27° and similarly at 55° to 56° are assigned to carbon (graphite) used for molding.

Preparation of Pentafluoroethane

Pentafluoroethane was prepared using catalysts 1 to 8 and comparative catalysts 1 to 3 obtained.

Examples 1 to 8

Using catalysts 1 to 8 obtained in said catalyst preparation, the gas phase fluorination of 1,1-dichloro-2,2,2-trifluoroethane (HCFC-123) by HF was conducted under the following reaction conditions.

Reaction conditions:

Catalyst: catalysts 1 to 8,

Catalyst amount: 9.2 g (uniform particle size between 300 and 1000 μm by grinding each pellet catalyst), Reaction tube: Hastelloy C, 15 mm inside diameter, Reaction gas (flow amount): HCFC-123 (48 NmL/min), HF (192 NmL/min), Reaction temperature: given in Table 3, and Reaction pressure: atmospheric.

After performing fluorination of HCFC-123 under the above reaction conditions, the gas obtained in the reactor outlet was washed, dried, and thereafter the composition of the organic substances was determined by gas chromatography analysis.

The results obtained are shown in the following Table 3. Here, "11X" in the Table illustrates the total concentration of CFC-112, CFC-112a, CFC-113, CFC-113a, CFC-114, CFC-114a and CFC-115 (hereinafter referred to as chlorofluoroethanes).

Further, the ratio of the pentafluorochloroethane (CFC-115) concentration to the pentafluoroethane (HFC-125) concentration and the ratio of the chlorofluoroethane (11X) concentration to the pentafluoroethane concentration as shown in Table shall be hereinafter referred to as [115/125] and [11X/125] respectively.

TABLE 3A

|  | Example | | | |
|---|---|---|---|---|
|  | 1 | 2 | 3 | 4 |
| Catalyst | Catalyst 1 | Catalyst 2 | Catalyst 3 | Catalyst 4 |
| Reaction Temperature (° C.) | 302 | 305 | 302 | 306 |
| Organic Substance Composition (Molar %) | | | | |
| HFC-125 | 11.1 | 11.9 | 12.2 | 11.8 |
| HCFC-124 | 47.0 | 46.6 | 46.7 | 46.8 |
| HCFC-123 | 41.8 | 41.4 | 40.9 | 41.3 |
| CFC-115 | 0.002 | 0.003 | 0.006 | 0.002 |
| 11x | 0.02 | 0.03 | 0.05 | 0.04 |
| Others | 0.07 | 0.11 | 0.13 | 0.09 |
| [115/125] (%) | 0.018 | 0.025 | 0.049 | 0.017 |
| [11X/125] (%) | 0.18 | 0.25 | 0.41 | 0.34 |

TABLE 3B

|  | Example | | | |
|---|---|---|---|---|
|  | 5 | 6 | 7 | 8 |
| Catalyst | Catalyst 5 | Catalyst 6 | Catalyst 7 | Catalyst 8 |
| Reaction Temperature (° C.) | 301 | 303 | 300 | 302 |
| Organic Substance Composition (Molar %) | | | | |
| HFC-125 | 12.4 | 12.4 | 11.9 | 12.0 |
| HCFC-124 | 46.7 | 46.5 | 46.8 | 46.7 |
| HCFC-123 | 40.8 | 40.9 | 41.2 | 41.2 |
| CFC-115 | 0.004 | 0.004 | 0.002 | 0.002 |
| 11x | 0.03 | 0.06 | 0.015 | 0.03 |
| Others | 0.09 | 0.12 | 0.06 | 0.08 |
| [115/125] (%) | 0.032 | 0.032 | 0.017 | 0.017 |
| [11x/125] (%) | 0.24 | 0.48 | 0.13 | 0.25 |

Comparative Examples 1 to 3

Using the catalysts of said comparative catalysts 1 to 3, the fluorination reaction of HFC-123 was conducted in reaction conditions similar to Examples 1 to 8. The results are shown in the following Table 4.

TABLE 4

| Catalyst | Comparative Example 1 Comparative Catalyst 1 | Comparative Example 2 Comparative Catalyst 2 | Comparative Example 3 Comparative Catalyst 3 |
|---|---|---|---|
| Reaction Temperature (° C.) | 300 | 334 | 340 |
| Organic Substance Composition (Molar %) | | | |
| HFC-125 | 12.1 | 12.0 | 11.9 |
| HCFC-124 | 46.4 | 46.6 | 46.4 |
| HCFC-123 | 41.0 | 40.6 | 41.0 |
| CFC-115 | 0.031 | 0.055 | 0.043 |
| 11X | 0.21 | 0.34 | 0.29 |
| Others | 0.34 | 0.49 | 0.41 |

TABLE 4-continued

| Catalyst | Comparative Example 1 Comparative Catalyst 1 | Comparative Example 2 Comparative Catalyst 2 | Comparative Example 3 Comparative Catalyst 3 |
|---|---|---|---|
| [115/125] (%) | 0.26 | 0.46 | 0.36 |
| [11X/125] (%) | 1.74 | 2.83 | 2.44 |

Examples 9 to 11

Using catalysts 1, 4 and 5, the gas phase fluorination reaction of 2-chloro-1,1,1,2-tetrafluoroethane (HCFC-124) by HF was conducted in the following conditions.

Reaction conditions:

Catalyst: catalysts 1, 4 and 5,

Catalyst amount: 18.5 g (uniform particle size between 300 and 1000 μm by grinding each pellet catalyst), Reaction tube: Hastelloy C, 15 mm inside diameter, Reaction gas (flow amount): HCFC-124 (55 NmL/min), HF (110 NmL/min), Reaction temperature: described in Table 5, and Reaction pressure: atmospheric.

After performing fluorination of HCFC-124 under the above reaction conditions, the gas obtained in the reactor outlet was washed, dried; thereafter, the composition of the organic substances was determined by gas chromatography analysis. The measurement results are shown in the following Table 5.

TABLE 5

| Catalyst | Example 9 Catalyst 1 | Example 10 Catalyst 4 | Example 11 Catalyst 5 |
|---|---|---|---|
| Reaction Temperature (° C.) | 318 | 319 | 316 |
| Organic Substance Composition (Molar %) | | | |
| HFC-125 | 66.4 | 65.2 | 66.8 |
| HCFC-124 | 21.2 | 23.9 | 20.8 |
| HCFC-123 | 12.2 | 10.7 | 12.2 |
| CFC-115 | 0.022 | 0.015 | 0.033 |
| 11X | 0.052 | 0.081 | 0.071 |
| Others | 0.13 | 0.14 | 0.11 |
| [115/125] (%) | 0.03 | 0.02 | 0.05 |
| [11X/125] (%) | 0.08 | 0.12 | 0.11 |

Comparative Examples 4 to 6

Using comparative catalysts 1 to 3, the fluorination reaction of HCFC-124 was conducted in reaction conditions similar to Examples 9, 10 and 11. The results are shown in the following Table 6.

TABLE 6

| Catalyst | Comparative Example 4 Comparative Catalyst 1 | Comparative Example 5 Comparative Catalyst 2 | Comparative Example 6 Comparative Catalyst 3 |
|---|---|---|---|
| Reaction Temperature (° C.) | 315 | 355 | 359 |

TABLE 6-continued

| Catalyst | Comparative Example 4 Comparative Catalyst 1 | Comparative Example 5 Comparative Catalyst 2 | Comparative Example 6 Comparative Catalyst 3 |
|---|---|---|---|
| Organic Substance Composition (Molar %) | | | |
| HFC-125 | 66.7 | 67.3 | 67.0 |
| HCFC-124 | 19.8 | 21.2 | 22.3 |
| HCFC-123 | 12.8 | 9.5 | 8.9 |
| CFC-115 | 0.110 | 0.210 | 0.220 |
| 11X | 0.25 | 0.72 | 0.68 |
| Others | 0.39 | 1.28 | 1.12 |
| [115/125] (%) | 0.16 | 0.31 | 0.33 |
| [11X/125] (%) | 1.37 | 1.07 | 1.01 |

In the cases of Examples 1 to 8 using catalysts 1 to 8 in tables 3 and 4 and using HCFC-123 as a starting gas, the amount of HCFC-124 produced which can be recycled is rich. On the contrary, both the amount of CFC-115 produced which is difficult to separate from the objective pentafluoroethane, and the amount of 11X produced which cannot be recycled and is highly loading on the environment, are less than Comparative Examples 1 to 3. In addition, these Examples have no significant difference between the amounts of the objective produced and are extremely useful methods of preparing pentafluoroethane in the industry.

Also Examples 9, 10 and 11 using HCFC-124 as the starting gas in Tables 5 and 6 are extremely useful methods of preparing pentafluoroethane in the industry, similar to the cases described above.

Comparative Examples 7 and 8

Herein, in the same reaction conditions (300° C.) as Comparative Example 1, the results [low major reactivity by the catalysts which have crystalline properties and the valence of the chromium is +3 (poor amounts of HCFC-124 and HFC-125 produced)] are shown when using comparative catalyst 2 [$Cr_2O_3$ (crystalline)], and when using comparative catalyst 3 [$Cr_2O_3$ (crystalline) with an added metal element (In)].

Namely, except for the 300° C. for the reaction temperature, the fluorination reaction of HCFC-123 was carried out under the same conditions as Comparative Examples 2 and 3. The results are shown in the following Table 7.

TABLE 7

| Catalyst | Comparative Example 7 Comparative Catalyst 2 | Comparative Example 8 Comparative Catalyst 3 |
|---|---|---|
| Reaction Temperature (° C.) | 300 | 300 |
| Organic Substance Composition (Molar %) | | |
| HFC-125 | 0.30 | 0.16 |
| HCFC-124 | 14.5 | 10.8 |
| HCFC-123 | 85.1 | 88.7 |
| CFC-115 | 0.002 | 0.001 |
| 11X | 0.069 | 0.041 |
| Others | 0.03 | 0.03 |
| [115/125] (%) | 0.67 | 0.63 |
| [115/125] (%) | 23.0 | 25.6 |

Namely, it is understood that, from the above results under the same conditions of uniform temperature, by using catalysts (crystalline property) having a chromium valence of +3, with or without added metals, the generation activity of the objective HFC-125 seriously deteriorates, compared with Comparative Example 1, and in addition the concentration of chlorofluoroethanes to HFC-125 rises. This demonstrates the superiority of amorphous chromium catalysts with high valences.

Examples 12–14

The Examples show results under conditions of higher temperature [the advantage (decrease of concentration of impurities in HFC-125) being that it is possible to lower the temperature owing to the high activation ( the catalysts of the present application)].

Except for the 350° C. for the reaction temperature, the fluorination reaction of HCFC-123 was carried out under the same conditions as Examples 1,2 and 7. The results are shown in the following Table 8.

TABLE 8

| Catalyst | Example 12 Catalyst 1 | Example 13 Catalyst 2 | Example 14 Catalyst 7 |
|---|---|---|---|
| Reaction Temperature (° C.) | 350 | 350 | 350 |
| Organic Substance Composition (Molar %) | | | |
| HFC-125 | 67.1 | 66.9 | 67.1 |
| HCFC-124 | 14.8 | 14.9 | 14.8 |
| HCFC-123 | 17.0 | 16.9 | 17.0 |
| CFC-115 | 0.11 | 0.17 | 0.12 |
| 11X | 0.28 | 0.33 | 0.26 |
| Others | 0.81 | 0.98 | 0.86 |
| [115/125] (%) | 0.16 | 0.25 | 0.18 |
| [11X/125] (%) | 0.42 | 0.49 | 0.39 |

From the above results, it is understood that the amount of HFC-125 produced increases by setting a higher temperature, and in addition the concentration of chlorofluoroethanes to HFC-125 rises, compared with examples using a lower temperature.

Example 15

Herein, the Example shows the case in which the organic substances obtained from a reactor are recycled (the preparation process of HFC-125 using the present inventive catalysts).

Figure 9:
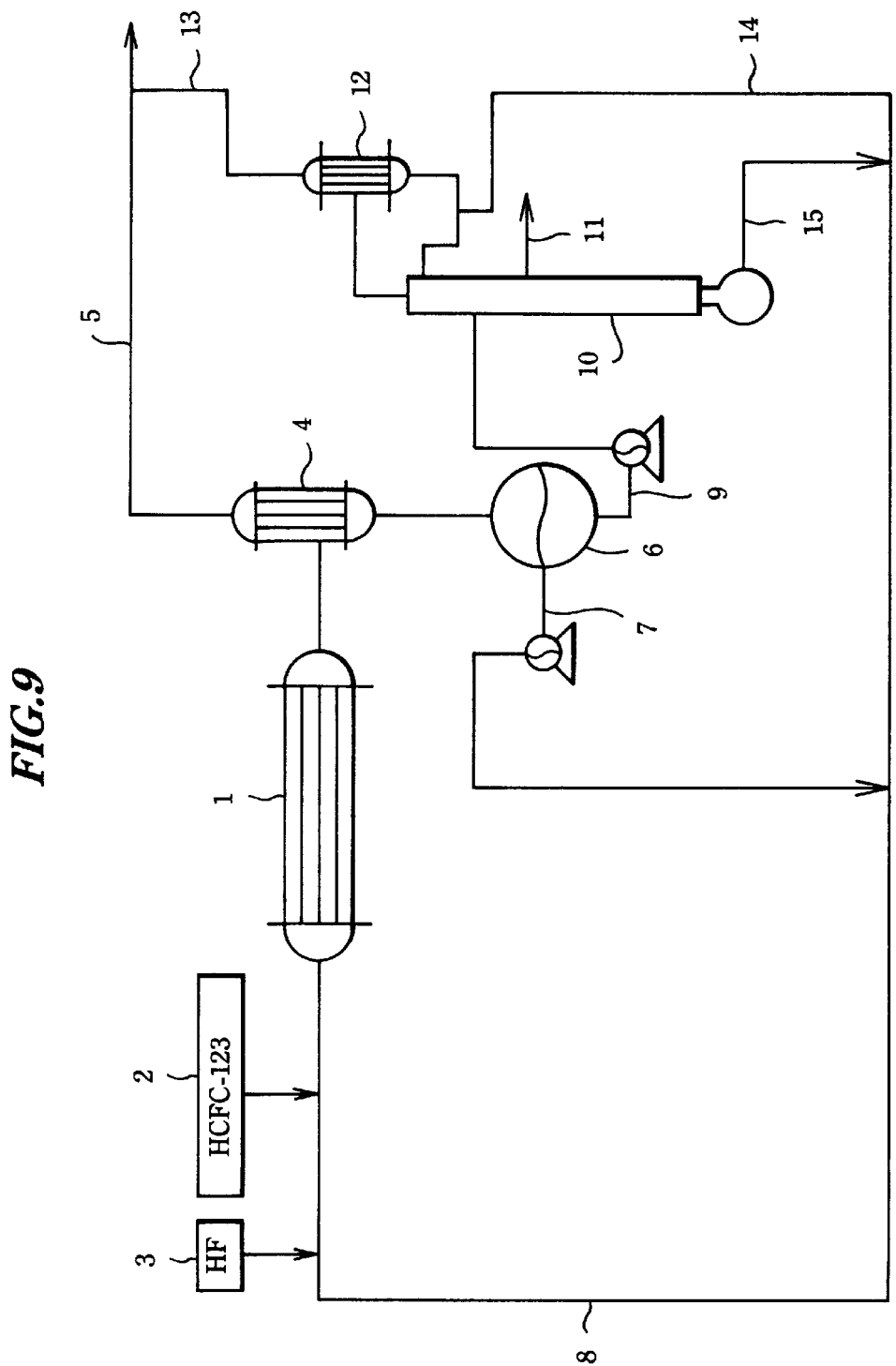
FIG. 9 is a process flowchart of recycling based on another Example of the present invention.

The present Example is illustrated based on the process flowchart illustrated in FIG. 9 as follows. First, 45 kg of fluorination catalyst 1 was charged into reactor 1 for gas phase fluorination, then HCFC-123 was supplied to this reactor 1 from material container 2 at a flow amount of 49 mol/hr followed by supplying anhydrous HF from material container 3 at a flow amount of 102 mol/hr. Further, the fluorination reaction in reactor 1 was set at a temperature of 324° C. at a pressure of 3.2 kg/cm$^2$.

Next, the reaction mixture which comes out of reactor 1 was introduced into partial condenser (heat exchanger) 4, then partially condensed into a non-condensate and a condensate at a temperature of –20° C. under a pressure of 3.1 kg/cm$^2$. The non-condensate mainly containing HFC-125 was recovered as the objective HFC-125 after being purified in a purification process through pipe 5. The condensate is sent into separating tank 6 and separated into a liquid containing mainly HF and a liquid containing mainly HCFC-123 and HCFC-124. The liquid containing mainly HF was again supplied to reactor 1 as the starting material through pipes 7 and 8. The liquid containing mainly HCFC-123 and HCFC-124 was introduced into distillation column 10 through pipe 9 followed by being distilled at a pressure of 7.2 kg/cm². The non-condensate in distillation column 10 and in condenser 12 located at the top portion contains mainly HFC-125. For the purification process, the non-condensate was sent through pipe 13 with the non-condensate from the partial condenser 4 described above and purified to give the objective HFC-125. The HCFC-124 accompanying the HFC-125 was returned again into distillation column 10.

The circulation substances in distillation column 10 through pipe 14 and the bottom components through pipe 15 as well as the liquid containing mainly HF, which was separated in separating tank 6, were supplied to reactor 1 through pipe 8, and were again used as the starting materials for the fluorination reaction together with newly added HCFC-123 and HF.

By continuing the above operation for 60 hr, the composition of each component became almost constant. The composition (flow amount: mol/hr) of each of the recovery substances (components from pipes 5 and 13) and of the recycling components (components from pipes 7, 14 and 15) in this step are shown in the following Table 9.

TABLE 9

|  | HPC-125 | HCFC-124 | CFC-114a | HCFC-123 | CFC-115 | HF | HCl |
|---|---|---|---|---|---|---|---|
| Recovery Substance | 40 | 20 | — | — | 0.11 | 4 | 98 |
| Recycling Component | 6 | 134 | 0.35 | 88 | — | 671 | — |

As is clear from the above results, the ratio of CFC-115 in HFC-125 in the recovery substances drawn from pipes 5 and 13 was about 0.22% and was quite small without the side cut (refer to Comparative Example 10 described later).

Comparative Example 9

Herein, the Comparative Example is illustrated using a chromium oxide catalyst (amorphous) without the addition of metals when recycling the organic substances obtained from the reactor.

Using comparative catalyst 1 charged into reactor 1, HFC-125 was prepared similarly according to Example 15 except that the reaction temperature was 320° C. Similarly according to Example 15, the composition (flow amount: mol/hr) of each of the recovery substances (components from pipes 5 and 13) and of the recycling components (components from pipes 7, 14 and 15) after 60 hr from the start of the reaction are shown in the following Table 10.

TABLE 10

|  | HPC-125 | HCFC-124 | CFC-114a | HCFC-123 | CFC-115 | HF | HCl |
|---|---|---|---|---|---|---|---|
| Recovery Substance | 49 | 20 | — | — | 0.6 | 4 | 98 |
| Recycling Component | 6 | 130 | 1.8 | 88 | — | 671 | — |

From the above results, the ratio of CFC-115 in HFC-125 in the recovery substances drawn from pipes 5 and 13 was about 1.22% and increased markedly, compared with that of Example 15.

Comparative Example 10

Herein, the preparation process of HFC-125 is illustrated when using the side cut in recycling.

HFC-125 was similarly prepared according to Comparative Example 9 except for the side cut of the component of the high concentration of CFC-114a in the middle of distillation column 10 out of the system through pipe 11. Similarly according to Example 15, the composition (flow amount: mol/hr) of each of the recovery substances (components from pipes 5 and 13), the recycling components (components from pipes 7, 14 and 15) and the side cut component (components from pipe 11) from the distillation column after 60 hr from the start of the reaction are shown in the following Table 11.

TABLE 11

|  | HPC-125 | HCFC-124 | CFC-114a | HCFC-123 | CFC-115 | HF | HCl |
|---|---|---|---|---|---|---|---|
| Recovery Substance | 49 | 20 | — | — | 0.1 | 4 | 98 |
| Recycling Component | 6 | 129 | 0.3 | 90 | — | 671 | — |
| Removal Component | — | 0.5 | 0.5 | 1.5 | — | — | — |

From the above results, the ratio of CFC-115 in HFC-125 in the recovery substances drawn from pipes 5 and 13 was about 0.2%. Accordingly, a similar effect as in Example 15 was obtained f or the purity of the product (HFC-12 5). However, the loss amount including CFC-115 was 2.6 mol/hr, an amount about 24 times that in Example 15 (0.1 mol/hr).

Comparative Examples 11 and 12

Herein, it is shown that the effect of decreasing the impure substances by adding metal elements to $Cr_2O_3$ (chromium valence: +3) is low, compared with the case of adding metals to the high valence chromium oxide in which the chromium is amorphous.

Comparative Catalyst 4

Figure 10:
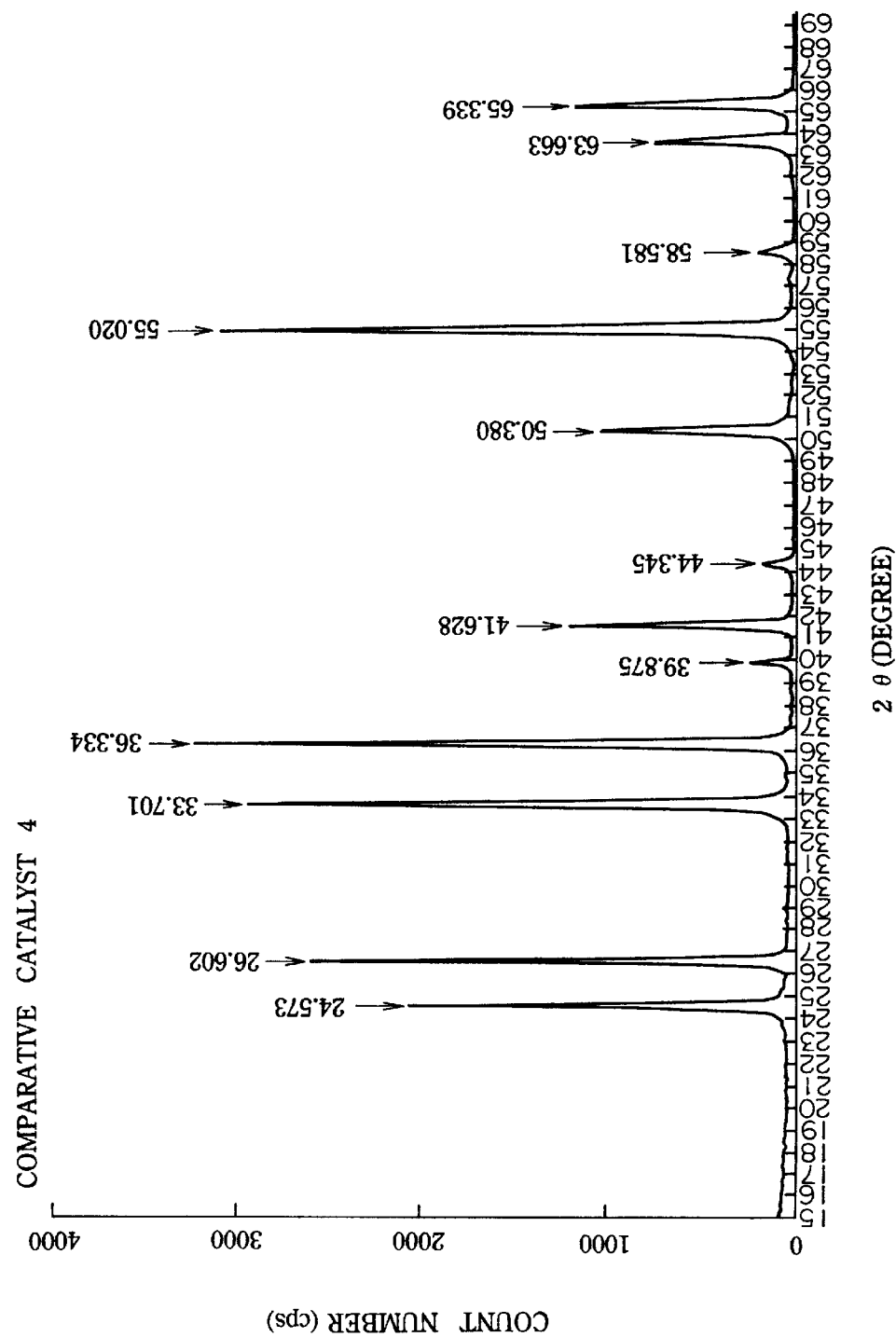
FIG. 10 is a graph showing the result of X-ray diffraction measurement of Comparative Catalyst 4.

Comparative catalyst 4 was prepared according to the same preparation method as for comparative catalyst 3 except for using 5.82 g of $Ga(NO_3)_3 \cdot 8H_2O$ instead of 5.16 g of $In(NO_3)_3 \cdot 3H_2O$. As for the valence of the catalyst obtained, the value from the composition analysis is +3.00 and the value determined from the magnetic susceptibility is +3.05. All the XRD diffraction peaks, shown in FIG. 10, were assigned to the crystal structure of $Cr_2O_3$.

Comparative Catalyst 5

Figure 11:
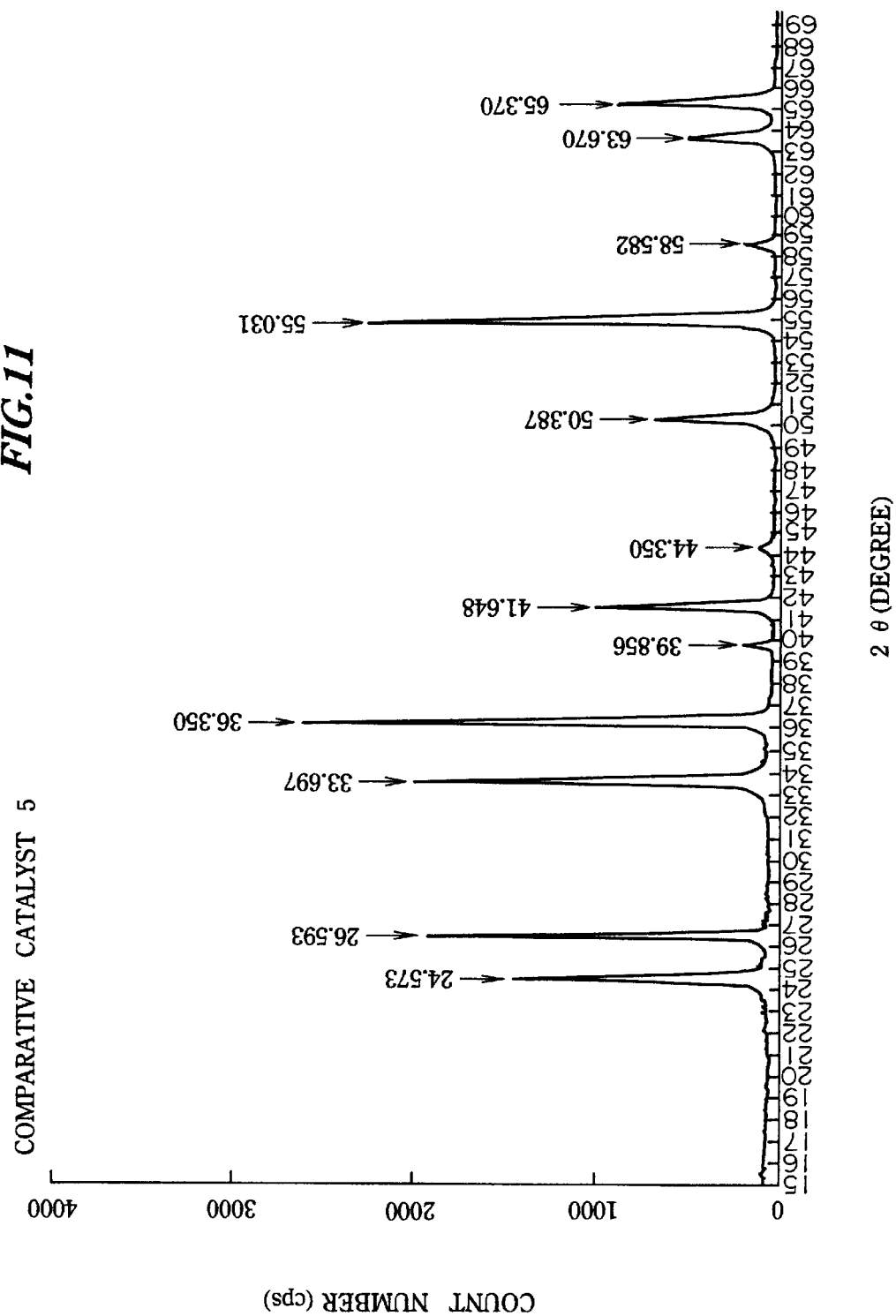
FIG. 11 is a graph showing the result of X-ray diffraction measurement of Comparative Catalyst 5.

Comparative catalyst 5 was prepared according to the same preparation method as for comparative catalyst 3 except for using 4.23 g of $Ni(NO_3)_2 \cdot 6H_2O$ instead of 5.16 g of $In(NO_3)_3 \cdot 3H_2O$. As for the valence of the catalyst obtained, the value from the composition analysis is +2.98 and the value determined from the magnetic susceptibility is +3.03. All the XRD diffraction peaks as, shown in FIG. 11, were assigned to the crystal structure of $Cr_2O_3$.

Using comparative catalysts 4 and 5, the fluorination reaction of HCFC-123 was conducted with the same reaction conditions as in Examples 1 to 8 (except for the reaction temperature). The results are shown in the following Table 12.

TABLE 12

|  | Comparative Example 11 | Comparative Example 12 |
|---|---|---|
| Catalyst | Comparative Catalyst 4 | Comparative Catalyst 5 |
| Reaction Temperature (° C.) | 343 | 344 |
| Organic Substance Composition (Molar %) | | |
| HFC-125 | 11.7 | 11.8 |
| HCFC-124 | 46.5 | 46.3 |
| HCFC-123 | 41.1 | 41.1 |
| CFC-115 | 0.050 | 0.057 |
| 11X | 0.33 | 0.37 |
| Others | 0.37 | 0.43 |
| [115/125](%) | 0.43 | 0.48 |
| [11X/125](%) | 2.82 | 3.14 |

From each of the results of Comparative Examples 2 and 3, Comparative Examples 5 and 6, Comparative Examples 7 and 8, or Comparative Examples 11 and 12, it is understood that the effect of decreasing the CFCs is small in the case of adding metals to crystalline catalysts of chromium with a valence of +3.

From the results of Example 1 to 11, it is also obvious that a marked decrease in CFCs concentration to HFC-125 is obtained by carrying metals on amorphous catalysts where the chromium valence is about +4.

Namely, as shown in the following Table 13, comparing the case of adding various metal elements to the chromium catalysts with a chromium valence of +3 with the case of not adding them, the decreased ratios of [CFC-115/HFC-125] and [11X/HFC-125] were 21% and 13%, respectively, at best, even if the metal elements were added. By adding metals, the ratios of [CFC-115/HFC-125] and [11X/HFC-125] occasionally increased.

On the other hand, when comparing the case of adding metal elements to the amorphous chromium catalysts with a chromium valence of +4 with the case of not adding them, the former case shows that the decreased ratios of [CFC-115/HFC-125] and [11X/HFC-125] reached 93% (at least 90%) and 90% (at least 80%), respectively, at best.

TABLE 13

| Added metal | Correspondence | [CFC-115/HFC-125] | [11X/HPC-125] |
|---|---|---|---|
| Crystalline Catalyst | | | |
| — | Comparative Example 2 | 0.46% | 2.83% |
| In | Comparative Example 3 | 0.36% (−21%) | 2.44% (−13%) |
| Ga | Comparative Example 11 | 0.43% (−6.5%) | 2.82% (−0.3%) |
| Ni | Comparative Example 12 | 0.48% (+4.3%) | 3.14% (+11%) |
| Amorphous Catalyst | | | |
| — | Comparative Example 1 | 0.26% | 1.74% |
| In | Example 1 | 0.028% (−93%) | 0.18% (−90%) |
| Ga | Example 2 | 0.025% (−90%) | 0.25% (−86%) |
| Ni | Example 4 | 0.017% (−93%) | 0.34% (−80%) |

*The values in parentheses show the decreased ratios of [CFC-115/HFC 125] and [11X/HFC-125], compared with the cases of catalysts without added metals.

What is claimed is:

1. Chromium catalysts for fluorination in an amorphous state wherein chromium compounds with at least one metal element added selected from the group composed of indium, gallium, cobalt, nickel, zinc and aluminum are contained as the main component, and average valence of the chromium in said chromium compounds is not less than +3.5 but not more than +5.0.

2. A catalysts for fluorination as claimed in claim 1 wherein said chromium compounds are at least one compound selected from the group composed of chromium oxide, chromium fluoride, fluorochromium oxide and chlorofluorochromium oxide.

3. A catalysts for fluorination as claimed in claim 2 which is fluorinated and for which the specific surface area after fluorination is within 25 $m^2/g$–130 $m^2/g$.

4. A catalysts for fluorination as claimed in claim 1 in which at least one element selected from the group composed of cadmium, magnesium and titanium having an improving effect on reactivity or selectivity is added.

5. A method of preparing catalysts for fluorination when the chromium catalysts in an amorphous state for fluorination are prepared and the main component of said chromium catalysts is chromium compounds with the addition of at least one metal element selected from the group composed of indium, gallium, cobalt, nickel, zinc and aluminum and the average valence of the chromium in said chromium compounds is not less than +3.5 but not more than +5.0, wherein chromium catalysts in said amorphous state for fluorination are obtained by calcination in an atmosphere of inert gas.

6. A method of preparing catalysts for fluorination as claimed in claim 5 therein said calcination is conducted at 380° C. to 410° C. for 0.5 hr to 3.5 hr in an atmosphere of inert gas.

7. A method of preparing catalysts for fluorination as claimed in claim 5 wherein said calcination is conducted after immersing chromium hydroxide in an aqueous solution of said metal elements followed by drying or said calcination is conducted after obtaining chromium hydroxide containing said metal elements by coprecipitation from an aqueous solution dissolving said metal elements and chromium followed by drying.

8. A method of preparing catalysts for fluorination as claimed in claim 5 wherein said chromium compounds are at least one compound selected from the group composed of chromium oxide, chromium fluoride, fluorochromium oxide and chlorofluorochromium oxide.

9. A method of preparing catalysts for fluorination as claimed in claim 8 wherein the specific surface area of said catalysts for fluorination is controlled within 25 $m^2/g$ to 130 $m^2/g$ by fluorinating after said calcination.

10. A method of preparing catalysts for fluorination as claimed in claim 5 wherein at least one element selected from the group composed of cadmium, magnesium and titanium having an improving effect on reactivity or selectivity is added to said catalysts for fluorination.

* * * * *